US006804558B2

(12) United States Patent
Haller et al.

(10) Patent No.: US 6,804,558 B2
(45) Date of Patent: Oct. 12, 2004

(54) SYSTEM AND METHOD OF COMMUNICATING BETWEEN AN IMPLANTABLE MEDICAL DEVICE AND A REMOTE COMPUTER SYSTEM OR HEALTH CARE PROVIDER

(75) Inventors: Markus Haller, Begnins (CH); Bozidar Ferek-Petric, Zagreb (HR); Adrianus P. Donders, Founex (CH)

(73) Assignee: Medtronic, Inc., Minneapolis, MN (US)

( * ) Notice: Subject to any disclaimer, the term of this patent is extended or adjusted under 35 U.S.C. 154(b) by 29 days.

(21) Appl. No.: 09/765,484

(22) Filed: Jan. 18, 2001

(65) Prior Publication Data

US 2002/0082665 A1 Jun. 27, 2002

Related U.S. Application Data

(63) Continuation of application No. 09/348,506, filed on Jul. 7, 1999.
(60) Provisional application No. 60/176,499, filed on Jan. 18, 2000.

(51) Int. Cl.[7] ............................................. A61N 1/362
(52) U.S. Cl. ............................. 607/30; 607/32; 607/60; 128/903
(58) Field of Search ......................... 600/300; 128/902, 128/903, 904; 607/60, 59, 30–32

(56) References Cited

U.S. PATENT DOCUMENTS

| 5,417,222 A | * | 5/1995 | Dempsey et al. ........... 128/903 |
| 5,683,432 A | | 11/1997 | Goedeke et al. |
| 5,697,959 A | | 12/1997 | Poore |
| 5,720,770 A | * | 2/1998 | Nappholz et al. ........... 128/903 |

(List continued on next page.)

FOREIGN PATENT DOCUMENTS

| EP | 0 987 047 | 9/1998 |
| EP | 062 082 | 6/1999 |
| EP | 062 083 | 6/1999 |
| EP | 062 084 | 6/1999 |
| EP | 062 085 | 6/1999 |
| EP | 062 086 | 6/1999 |
| EP | 062 976 | 6/1999 |
| EP | 062 980 | 6/1999 |
| EP | 062 981 | 6/1999 |
| WO | WO97/00708 | 1/1997 |
| WO | WO99/14882 | 3/1999 |

OTHER PUBLICATIONS

"Nokia Launches Nokia 9000 Communicator", Mar. 12, 1997.*
"Qualcomm merges phone, handheld", Sep. 21, 1998.*
Arzbaecher et al., "Automatic Tachycardia Recognition," PACE, 541–547 (May–Jun. 1984).
Olson et al., "Onset and Stability for Ventricular Tachyarrhythmia Detection in an Implantable Pacer–Cardioverter–Defibrillator," Computers in Cardiology, IEEE Computer Society Press, 167–170 (Oct. 7–10, 1986).

Primary Examiner—George R. Evanisko
(74) Attorney, Agent, or Firm—Girma Wolde-Michael; Daniel G. Chapik

(57) ABSTRACT

A medical information communication system and corresponding methods are described. The system permits monitoring the performance of an implantable medical device (IMD) implanted within a body of a patient, monitoring the health of the patient, or remotely delivering a therapy to the patient through the IMD. The IMD is capable of bi-directional communication with a communication module, a mobile telephone and/or a Personal Data Assistant (PDA) located outside the patient's body. The system may comprise the IMD, the communication module and/or a mobile telephone and/or a PDA, a remote computer system, and a communication system capable of bi-directional communication, where the communication module, the mobile telephone and/or the PDA are capable of receiving information from the IMD or relaying information thereto.

4 Claims, 23 Drawing Sheets

U.S. PATENT DOCUMENTS

| | | |
|---|---|---|
| 5,720,771 A | 2/1998 | Snell |
| 5,722,999 A | 3/1998 | Snell |
| 5,749,907 A | 5/1998 | Mann |
| 5,752,235 A | 5/1998 | Demenus et al. |
| 5,752,976 A | 5/1998 | Duffin et al. |
| 5,791,342 A | 8/1998 | Woodard |
| 5,800,473 A | 9/1998 | Faisandier |
| 5,839,438 A | 11/1998 | Craettinger et al. |
| 5,843,139 A | 12/1998 | Goedeke et al. |
| 5,848,593 A | 12/1998 | McGrady et al. |
| 5,855,609 A | 1/1999 | Knapp |
| 5,857,967 A | 1/1999 | Frid et al. |
| 5,876,351 A | 3/1999 | Rohde |
| 5,895,371 A | 4/1999 | Levital et al. |
| 5,912,818 A | 6/1999 | McGrady et al. |
| 5,941,906 A | 8/1999 | Barreras, Sr. et al. |
| 5,944,659 A | 8/1999 | Flach et al. |
| 5,954,641 A | 9/1999 | Kehr et al. |
| 5,971,593 A | 10/1999 | McGrady |
| 5,974,124 A | 10/1999 | Schlueter, Jr. et al. |
| 5,977,431 A | 11/1999 | Knapp et al. |
| 5,987,519 A | 11/1999 | Peifer et al. |
| 5,993,046 A | 11/1999 | McGrady et al. |
| 6,004,020 A | 12/1999 | Bartur |
| 6,006,035 A | 12/1999 | Nabahi |
| 6,022,315 A | 2/2000 | Iliff |
| 6,023,345 A | 2/2000 | Bloomfield |
| 6,024,539 A | 2/2000 | Blomquist |
| 6,025,931 A | 2/2000 | Bloomfield |
| 6,035,328 A | 3/2000 | Soukal |
| 6,053,887 A | 4/2000 | Levitas et al. |
| 6,083,248 A | 7/2000 | Thompson et al. |
| 6,117,073 A * | 9/2000 | Jones et al. .................. 600/300 |
| 6,292,698 B1 * | 9/2001 | Duffin et al. .................. 607/32 |
| 6,305,377 B1 * | 10/2001 | Portwood et al. ........... 128/897 |
| 2001/0032099 A1 * | 10/2001 | Joao .............................. 705/2 |
| 2001/0047125 A1 * | 11/2001 | Quy ........................... 600/300 |
| 2002/0002326 A1 * | 1/2002 | Causey III et al. ......... 600/300 |

* cited by examiner

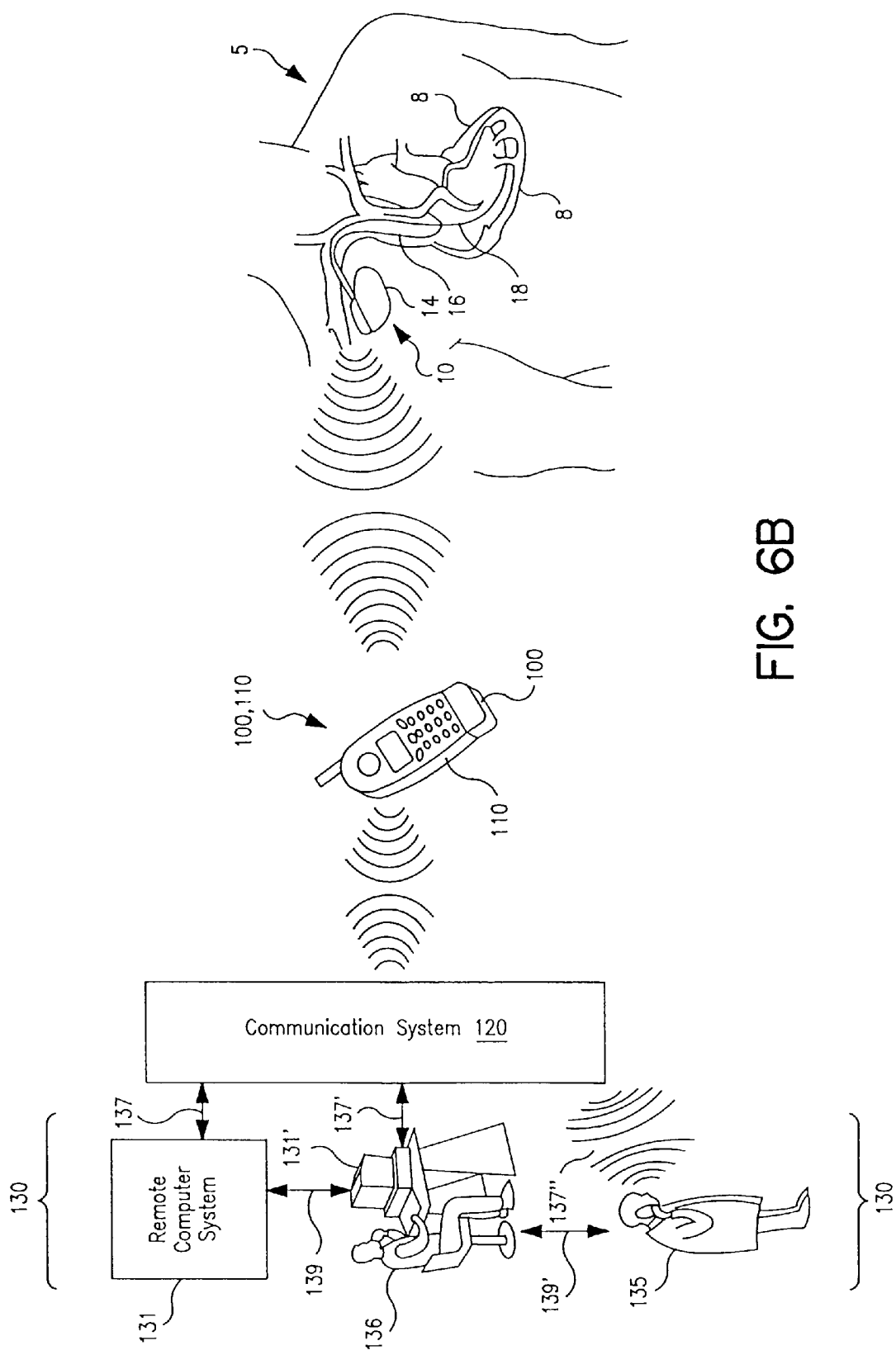

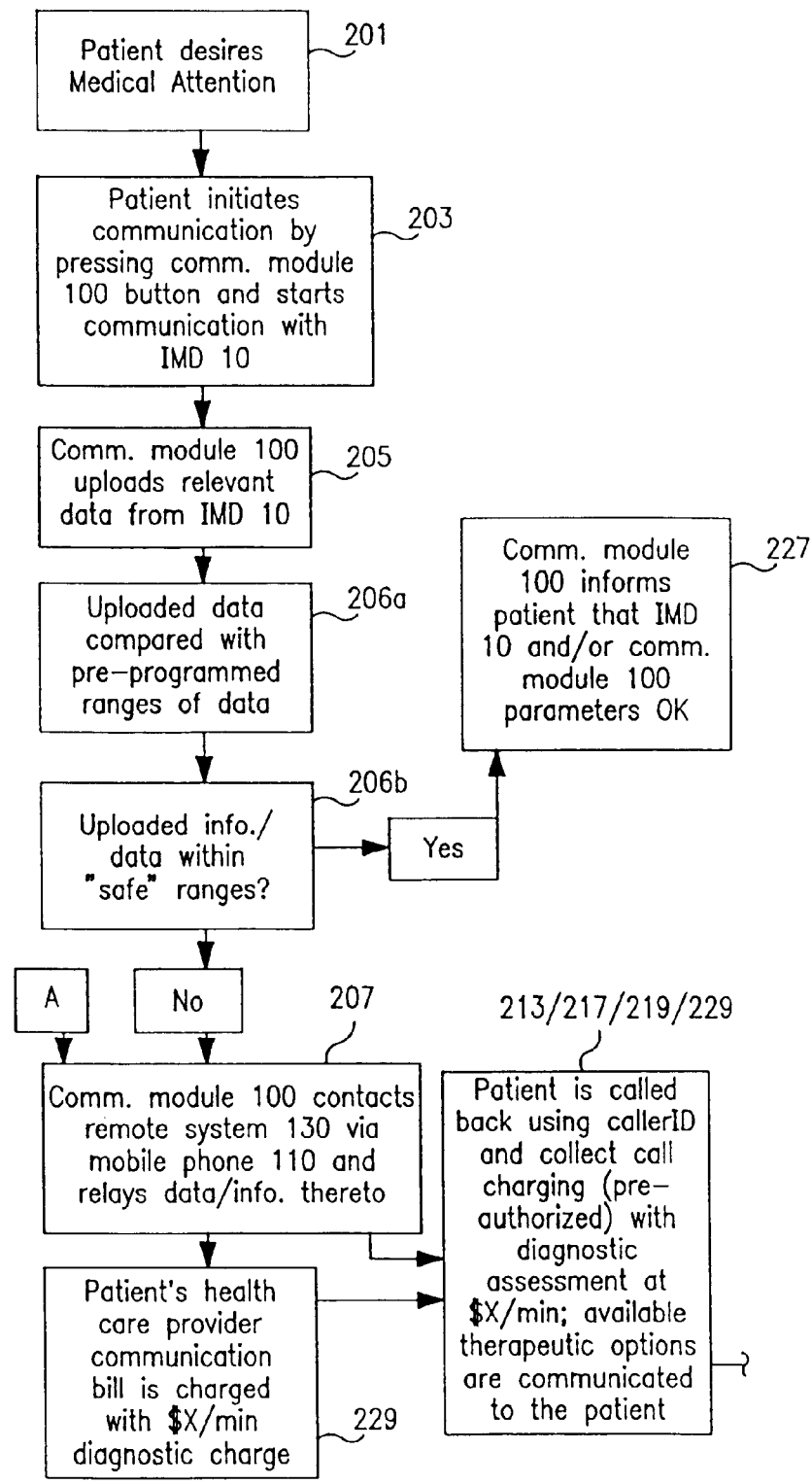
FIG. 9C-I

SYSTEM AND METHOD OF COMMUNICATING BETWEEN AN IMPLANTABLE MEDICAL DEVICE AND A REMOTE COMPUTER SYSTEM OR HEALTH CARE PROVIDER

RELATED PATENT APPLICATIONS

This patent application claims priority and other benefits from U.S. Provisional Patent Application Ser. No. 60/176,499 entitled "Method and System for Patient Controlled Data Exchange between Physician and Implanted Device" to Haller et al. filed Jan. 18, 2000, and incorporates the entirety of same by reference herein. This patent application is also a continuation-in-part of U.S. patent application Ser. No. 09/348,506 entitled "System for Remote Communication with a Medical Device" to Ferek-Petric filed Jul. 7, 1999, and incorporates the entirety of same by reference herein.

Also incorporated by reference herein, each in its respective entirety, are the following pending U.S. patent applications: (1) U.S. patent appln. Ser. No. 09/430,208 filed Oct. 29, 2000 for "Automatic Invoice upon Pacemaker Implant" to Linberg; (2) U.S. patent appln. Ser. No. 09/466,284 filed Dec. 17, 1999 for "A Virtual Electrophysiologic Value-Added Service for Cardiac Rhythm" to Linberg et al.; (3) U.S. patent appln. Ser. No. 09/437,615 filed Nov. 10, 1999 for "Method for Remote Delivery of Software-Based Training with Automated Support for Certification and Enabling Software Applications on Programmers" to Linberg; (4) U.S. patent appln. Ser. No. 09/426,741 filed Oct. 26, 1999 for "Remote Troubleshooting and Preventive Maintenance of Programmers" to Linberg; (5) U.S. patent appln. Ser. No. 09/429,960 filed Oct. 29, 1999 for "Method to Automate Remote Medical Instrument Updates"" to Linberg; and (6) U.S. patent appln. Ser. No. 09/429,956 filed Oct. 29, 1999 for "Electronic Self-Identification of Medical Instruments and Smart Peripherals" to Linberg.

FIELD OF THE INVENTION

The present invention relates generally to medical device systems, and more particularly relates to a system and method for communication between an IMD and a remote computer and/or health care provider employing a mobile telephone and a communication module linked thereto.

BACKGROUND OF THE INVENTION

An ideal technology-based health care system would be capable of fully integrating the technical and social aspects of patient care and therapy and permit a patient or a medical device implanted within the patient to communicate a remote computer system or health care provider irrespective of the location of the patient, the remote computer system or the health care provider. While clinicians will continue to treat patients in accordance with accepted modem medical practice, developments in communications technology are making it ever more possible to provide medical services in a time and place independent manner.

Prior art methods of providing clinical medical services are generally limited to in-hospital or in-clinic procedures. For example, if a physician must review the performance parameters of an implantable medical device (hereinafter "IMD") in a patient, it is likely the patient will have to visit a clinic or hospital where the review can accomplished. If the medical conditions of a patient having an IMD warrant continuous monitoring or adjustment of the device, the patient may have to remain at the hospital. Such continued treatment poses economic and social problems. Additionally, patients' physical movements are restricted and patients are inconvenienced by the need to visit or stay in a hospital or a clinic. As the proportion of the population with implanted medical devices increases, ever more hospitals, clinics and service personnel will be required to provide in-hospital or in-clinic services to such patients, thus escalating healthcare costs.

In accordance with prior art practice, most patient having IMDs are required to visit a clinical center for occasional retrieval of data therefrom. Typically, the IMD's performance is assessed and patient data are acquired for clinical and research purposes. Such data is usually acquired by having the patient visit a hospital or clinic where data stored in the memory of the IMD is uploaded to a programmer. Depending on the frequency of data acquisition and storage, this procedure can result in difficulty and inconvenience for patients living in rural areas or having limited physical mobility. Similarly, if the software in an IMD must be updated, the patient is required to come into a clinic or hospital to have the upgrade installed.

The prior art discloses various types of remote sensing and communication systems that interact with IMDs. One such system is disclosed in Funke, U.S. Pat. No. 4,987,897. This patent discloses a system that is at least partially implanted into a living body with a minimum of two implanted devices interconnected by a communication transmission channel. The invention further discloses wireless communications between an external medical device/programmer and an implanted device.

Another example of a prior art sensing and communication system is disclosed by Strandberg in U.S. Pat. No. 4,886,064. In this patent, body activity sensors, such as temperature, motion, respiration and/or blood oxygen sensors, are positioned in a patient's body outside a pacer capsule. The sensors wirelessly transmit body activity signals, which are processed by circuitry in the heart pacer. The heart pacing functions are influenced by the processed signals. The signal transmission is a two-way network and allows the sensors to receive control signals for altering the sensor characteristics.

In U.S. Pat. No. 4,494,950, Fischell discloses a system consisting of a plurality of separate modules that collectively perform a useful biomedical purpose. The modules communicate electromagnetically with one another without the use of interconnecting wires. Physiologic sensor measurements sent from a first-module cause a second module to perform some function in a closed loop manner.

One example of remote monitoring of implanted cardioverter defibrillators is U.S. Pat. No. 5,321,618 to Gessman, where a remote apparatus is adapted to receive commands from and transmit data to a central monitoring facility over telephone communication channels. The remote apparatus includes equipment for acquiring a patient's ECG and transmitting same to the central facility using telephone communications channels. The remote apparatus also includes a segment, responsive to a command received from the central monitoring facility, for enabling the emission of audio tone signals from the cardioverter defibrillator. The audio tones are detected and sent to the central monitoring facility via the telephone communication channel. The remote apparatus also includes patient alert devices, which are activated by commands received from the central monitoring facility over the telephone communication channel.

An additional example of prior art practice includes a packet-based telemedicine system for communicating information between central monitoring stations and a remote patient monitoring station disclosed by Pfeiffer in WO 99/14882 published Mar. 25, 1999. This disclosure relates to a packet-based telemedicine system for communicating video, voice and medical data between a central monitoring station and a patient that is remotely located with respect to the central monitoring station. The patient monitoring station obtains digital video, voice and medical measurement data from a patient and encapsulates the data in packets and sends the packets over a network to the central monitoring station. Since the information is encapsulated in packets, the information can be sent over multiple types or combination of network architectures, including a community access television (CATV) network, the public switched telephone network (PSTN), the integrated services digital network (ISDN), the Internet, a local area network (LAN), a wide area network (WAN), over a wireless communications network, or over asynchronous transfer mode (ATM) network. A separate transmission code is not required for each different type of transmission media.

Another example of a telemetry system for IMDs is disclosed by Duffin et al. in U.S. Pat. No. 5,752,976. The Duffin disclosure relates to a system-and method for communicating with a medical device implanted in an ambulatory patient and for locating the patient in order to selectively monitor device function from a remote medical support network. The communications link between the medical support network and the patient communications control device may comprise a world wide satellite network, a cellular telephone network or other personal communications system.

Thompson et al. disclose a patient tracking system in U.S. Pat. Nos. 6,083,248 and 5,752,976 entitled "World-wide Patient Location and Data Telemetry System For IMDs". Thompson et al. also describe features for patient tracking in a mobile environment worldwide via the GPS system.

Ferek-Petric discloses a system for communication with a medical device in co-pending U.S. patent application Ser. No. 09/348,506 entitled "System for Remote Communication with a Medical Device" filed Jul. 7, 1999. Ferek-Petric's disclosure relates to a system that permits remote communications with a medical device, such as a programmer. Experts provide guidance and support to remote service personnel or operators located at the programmer. The system may include a medical device adapted to be implanted into a patient; a server PC communicating with the medical device; the server PC having means for receiving data transmitted across a dispersed data communication pathway, such as the Internet; and a client PC having means for receiving data transmitted across a dispersed communications pathway from the SPC. In certain configurations the server PC may have means for transmitting data across a dispersed data communication pathway (Internet) along a first channel and a second channel; and the client PC may have means for receiving data across a dispersed communication pathway from the server PC along a first channel and a second channel.

Ferek-Petric further discloses the implementation of communication systems associated with IMDs that are compatible with the Internet. The communications scheme is structured primarily to alert remote experts to existing or impending problems with the programming device so that prudent action, such as early maintenance or other remedial steps, may be exercised in a timely manner. Further, because of the early warning or advance knowledge of the problem, the remote expert would be well informed to provide remote advice or guidance to service personnel or operators at the programmer.

In U.S. Pat. No. 5,800,473, Faisandier et al. provide a system and method for the automatic update of the software of an external programmer implant that is used to program and configure an active IMD implant and acquire data obtained by the implant. The programmer comprises software composed of an assembly of software objects. The implant comprises a memory containing parametric data for the functioning of the implant and an assembly of software objects necessary for the functioning of the programmer in connection with the parametric data.

In U.S. Pat. No. 5,772,586 to Heinonen et al., there is disclosed a method for monitoring the health of a patient by utilizing measurements. The measurements are supplied via a communication device utilizing a wireless data transmission link to a data processing system available to the person monitoring the patient's health. The patient's health is monitored by means of the data stored in the data processing system.

In EP 0 987 047 A2 to Lang et al. entitled "Patient Monitoring System" having a priority date of Sep. 18, 1998, there is a description of sensing and acquiring physiological data with a pacemaker or defibrillator, and transmitting those data by mobile phone to an external system accessible by a cardiologist. The cardiologist may then evaluate the data and initiate emergency action such ordering an ambulance. The mobile phone may also be employed to determine the patient's geographical location, as well as to transmit a signal warning of a low state of charge in the pacemaker or defibrillator battery.

It will now be seen that there exist many unfulfilled needs to more easily, quickly and cost-effectively monitor and control the performance of an IMD in a patient on a regular or continuous basis, where the patient is not required to visit a health care facility or a health care provider in person when the monitoring is undertaken. It will also now be seen that there exist many unfulfilled needs to more easily, quickly and cost effectively monitor and control the health of a patient having an IMD on a regular or continuous basis, where the patient is not required to visit a health care facility or a health care provider in person when the monitoring is undertaken. Ambulatory patients suffering from atrial fibrillation, chronic pain, bradycardia, syncope, tachycardia and other maladies treated with IMDs need a tool to communicate with their physicians or other health care providers when they want to. There are now over 2.5 million ambulatory implantable pacemaker patients, virtually all of whom must visit a clinic or hospital to have their health status or pacemaker performance checked.

Patents and printed publications describing various aspects of the foregoing problems and the state of the art are listed below.

TABLE 1

PATENTS

| U.S. or Foreign Patent or Patent Application/Publication No. | Inventor(s) | Issue Date or Foreign Priority Date |
| --- | --- | --- |
| U.S. Pat. No. 4,494,950 | Fischell | Jan. 22, 1985 |
| U.S. Pat. No. 4,531,523 | Anderson | Jul. 30, 1985 |
| U.S. Pat. No. ,531,527 | Reinhold, JR. et al. | Jul. 30, 1985 |
| U.S. Pat. No. 4,768,176 | Kehr et al. | Aug. 30, 1988 |
| U.S. Pat. No. 4,768,177 | Kehr et al. | Aug. 30, 1988 |
| U.S. Pat. No. 4,886,064 | Strandberg | Dec. 12, 1989 |
| U.S. Pat. No. 4,987,897 | Funke | Jan. 29, 1991 |

TABLE 1-continued

PATENTS

| U.S. or Foreign Patent or Patent Application/Publication No. | Inventor(s) | Issue Date or Foreign Priority Date |
|---|---|---|
| U.S. Pat. No. 5,047,948 | Turner | Sept. 10, 1991 |
| U.S. Pat. No. 5,100,380 | Epstein et al. | Mar. 31, 1992 |
| U.S. Pat. No. 5,113,869 | Nappholz et al. | May 19, 1992 |
| U.S. Pat. No. 5,172,698 | Stanko | Dec. 22, 1992 |
| U.S. Pat. No. 5,200,891 | Kehr et al. | Apr. 6, 1993 |
| U.S. Pat. No. 5,226,425 | Righter | Jul. 13, 1993 |
| U.S. Pat. No. 5,321,618 | Gessman | Jun. 14, 1994 |
| U.S. Pat. No. 5,336,245 | Adams Theodore P et al. | Aug. 9, 1994 |
| U.S. Pat. No. 5,338,157 | Blomquist | Aug. 16, 1994 |
| U.S. Pat. No. 5,354,319 | Blomquist | Oct. 11, 1994 |
| U.S. Pat. No. 5,369,699 | Page et al. | Nov. 29, 1994 |
| U.S. Pat. No. 5,400,246 | Wilson et al. | Mar. 21, 1995 |
| U.S. Pat. No. 5,522,396 | Langer et al. | Jun. 4, 1996 |
| U.S. Pat. No. 5,526,630 | Markowitz et al. | May 6, 1997 |
| U.S. Pat. No. 5,573,506 | Vasko | Nov. 12, 1996 |
| U.S. Pat. No. 5,582,593 | Hultman | Dec. 10, 1996 |
| U.S. Pat. No. 5,619,991 | Sloane | Apr. 15, 1997 |
| U.S. Pat. No. 5,634,468 | Platt et al. | Jun. 3, 1997 |
| U.S. Pat. No. 5,642,731 | Kehr | Jul. 1, 1997 |
| U.S. Pat. No. 5,643,212 | Coutre et al. | Jul. 1, 1997 |
| U.S. Pat. No. 5,678,562 | Sellers | Oct. 21, 1997 |
| U.S. Pat. No. 5,683,432 | Goedeke et al. | Nov. 4, 1997 |
| U.S. Pat. No. 5,697,959 | Poore | Dec. 16, 1997 |
| U.S. Pat. No. 5,719,761 | Gatti et al. | Feb. 17, 1998 |
| U.S. Pat. No. 5,720,770 | Nappholz et al. | Feb. 24, 1998 |
| U.S. Pat. No. 5,720,771 | Snell | Feb. 24, 1998 |
| U.S. Pat. No. 5,722,999 | Snell | Mar. 3, 1998 |
| U.S. Pat. No. 5,749,907 | Mann | May 12, 1998 |
| U.S. Pat. No. 5,752,235 | Demenus et al. | May 12, 1998 |
| U.S. Pat. No. 5,752,976 | Duffin et al. | May 19, 1998 |
| U.S. Pat. No. 5,791,342 | Woodard | Aug. 11, 1998 |
| U.S. Pat. No. 5,800,473 | Faisandier | Sep. 1, 1998 |
| U.S. Pat. No. 5,839,438 | Craettinger et al. | Nov. 24, 1998 |
| U.S. Pat. No. 5,843,138 | Goedeke et al. | Dec. 1, 1998 |
| U.S. Pat. No. 5,848,593 | Mcgrady et al. | Dec. 15, 1998 |
| U.S. Pat. No. 5,855,609 | Knapp | Jan. 5, 1999 |
| U.S. Pat. No. 5,857,967 | Frid et al. | Jan. 12, 1999 |
| U.S. Pat. No. 5,876,351 | Rohde | Mar. 2, 1999 |
| U.S. Pat. No. 5,895,371 | Levital et al. | Apr. 20, 1999 |
| U.S. Pat. No. 5,912,818 | McGrady et al. | Jun. 15, 1999 |
| U.S. Pat. No. 5,941,906 | Barreras Sr. et al. | Aug. 24, 1999 |
| U.S. Pat. No. 5,944,659 | Flach et al. | Aug. 31, 1999 |
| U.S. Pat. No. 5,954,641 | Kehr et al. | Sep. 21, 1999 |
| U.S. Pat. No. 5,971,593 | McGrady | Oct. 26, 1999 |
| U.S. Pat. No. 5,974,124 | Schlueter, Jr. et al. | Oct. 26, 1999 |
| U.S. Pat. No. 5,977,431 | Knapp et al. | Nov. 2, 1999 |
| U.S. Pat. No. 5,987,519 | Peifer et al. | Nov. 16, 1999 |
| U.S. Pat. No. 5,993,046 | McGrady et al. | Nov. 30, 1999 |
| U.S. Pat. No. 6,004,020 | Bartur | Dec. 21, 1999 |
| U.S. Pat. No. 6,006,035 | Nabahi | Dec. 21, 1999 |
| U.S. Pat. No. 6,022,315 | Iliff | Feb. 8, 2000 |
| U.S. Pat. No. 6,023,345 | Bloomfield | Feb. 8, 2000 |
| U.S. Pat. No. 6,024,539 | Blomquist | Feb. 15, 2000 |
| U.S. Pat. No. 6,025,931 | Bloomfield | Feb. 15, 2000 |
| U.S. Pat. No. 6,035,328 | Soukal | Mar. 7, 2000 |
| U.S. Pat. No. 6,053,887 | Levitas et al. | Apr. 25, 2000 |
| WO 99/14882 | Pfeifer et al. | Mar. 25, 1999 |
| WO 97/00708 | Duffin et al. | Jan. 9, 1997 |
| EP 0 987 047 A2 | Lang et al. | Sept. 18, 1998 |
| EP 062 976 A2 | Schaldach et al. | Jun. 26, 1999 |
| EP 062 980 A2 | Kraus et al. | Jun. 25, 1999 |
| EP 062 981 A2 | Kraus et al. | Jun. 25, 1999 |
| EP 062 982 A2 | Kraus et al. | Jun. 25, 1999 |
| EP 062 983 A2 | Kraus et al. | Jun. 25, 1999 |
| EP 062 984 A2 | Kraus et al. | Jun. 25, 1999 |
| EP 062 985 A2 | Kraus et al. | Jun. 25, 1999 |
| EP 062 986 A2 | Lorkowski et al. | Jun. 25, 1999 |

All patents and printed publications listed hereinabove are hereby incorporated by reference herein, each in its respective entirety. As those of ordinary skill in the art will appreciate readily upon reviewing the drawings set forth herein and upon reading the Summary of the Invention, Detailed Description of the Preferred Embodiments and Claims set forth below, at least some of the devices and methods disclosed in the patents and publications listed hereinabove may be modified advantageously in accordance with the teachings of the present invention.

SUMMARY OF THE INVENTION

Various embodiments of the present invention have certain objects. That is, various embodiments of the present invention provide solutions to problems existing in the prior art, including, but not limited to, problems such as: (a) requiring patients having IMDs to visit a hospital or clinic for routine monitoring of the patient's health; (b) requiring patients having IMDs to visit a hospital or clinic for routine monitoring of the IMD's performance; (c) requiring patients having IMDs to visit a hospital or clinic when the IMD is to be re-programmed; (d) relatively long periods of time passing (e.g., hours, days or even weeks) between the time a patient first detects a problem with the operation of an IMD or the patient's health on the one hand, and the time the problem is actually diagnosed and/or acted upon by a physician or other health care professional on the other hand; (e) IMD performance monitoring being relatively expensive owing to patients being required to visit a clinic or hospital; (f) monitoring of patients having IMDs being relatively expensive owing to patients being required to visit a clinic or hospital; (g) existing remote patient monitoring telephony systems being expensive, bulky, unwieldy, stationary, and limited in application; (h) existing remote IMD monitoring telephony systems being expensive, bulky, unwieldy, stationary, and limited in application; (i) complicated, expensive, non-uniform and time-consuming billing, invoicing and reimbursement systems for medical services rendered.

Various embodiments of the present invention have certain advantages, including, without limitation, one or more of: (a) reducing, if not eliminating, the requirement for a patient having an IMD to visit a clinic or a hospital for routine check-ups or monitoring of the IMD; (b) substantially reducing costs associated with monitoring patients having IMDs; (c) substantially reducing costs associated with monitoring the performance of IMDs; (d) providing a patient having an IMD with the ability to contact a health care provider or health care provider service almost instantly in respect of the patient's current health status; (e) providing a patient with the ability to contact a health care provider or health care provider service almost instantly in respect of the performance of the IMD; (f) providing a patient having an IMD with the ability to contact a health care provider or health care provider service in respect of the patient's current health status from almost any location; (g) providing a patient having an IMD with the ability to contact a health care provider or health care provider service in respect of the performance of the IMD from almost any location; (h) providing a health care provider or service provider with the ability to contact almost instantly a patient having an IMD in respect of the patient's current health status; (I) providing a health care provider or service provider with the ability to contact almost instantly a patient having an IMD in respect of the performance of the IMD; (j) providing a health care provider or service provider with the ability to contact a patient located almost anywhere having an IMD in respect of the patient's current health status; (k) providing a health care provider or service provider with the ability to contact a patient located almost anywhere having an IMD in respect of the performance of the IMD; (l) providing a health care provider or service provider with the ability to re-program an IMD located almost anywhere; (m) providing a health care provider or service provider with the ability to quickly download new software to an IMD located almost anywhere; (n) providing a health care provider or service provider, or a patient having an IMD, to contact an emergency medical service quickly in the event monitoring of the patient or the IMD reveals such a service is required; (o) providing a computer system with the ability to automatically and quickly contact an emergency medical service in the event monitoring of the patient or the IMD reveals such a service is required; (p) enabling remote software debugging, analysis, troubleshooting, maintenance and upgrade of the IMD or the communication module, and (q) generating medical service invoices automatically and efficiently.

Various embodiments of the present invention have certain features, including one or more of the following: (a) a communication module, separate from, connectable to, or integral with a mobile telephone, the module being capable of communicating with an IMD and the mobile telephone; (b) a communication module capable of communicating with an IMD and a mobile telephone comprising a microprocessor, a controller or other CPU, computer readable memory operable connected to the microprocessor, controller or CPU, and at least one RF or other suitable type of communications circuit for transmitting information to and receiving information from the IMD; (c) a communication module capable of communicating with an IMD and a mobile telephone comprising a data output port, cable and connector for connection to a mobile telephone data input port; (d) a communication module capable of communicating with an IMD and a mobile telephone comprising computer readable software for initiating and maintaining communications with a mobile telephone using standardized handshake protocols; (e) a communication module capable of communicating with an IMD and a mobile telephone comprising at least one of: a telemetry signal strength indicator, a telemetry session success indicator; a computer readable medium (such as volatile or non-volatile RAM, ROM, EEPROM, a hard or floppy disk, flash memory, and so on) for storing patient data and/or IMD data and/or software; a real-time clock; a battery; a serial output interface; a parallel output interface; (f) a communication module capable of communicating with an IMD and a mobile telephone, the module being electrically powered by a portable energy source such as a battery located in, or connected or attached to the mobile phone, or alternatively being electrically powered by its own portable energy source or household line ac power; (g) a communication module capable of communicating with an IMD and a mobile telephone, the module being plug-and-play compatible with the mobile telephone; (h) a communication module capable of communicating with an IMD and a mobile telephone, the module, upon receiving instruction from a patient having the medical device implanted therein, interrogating the implantable device to assess operational performance of the device and/or the health status of the patient, the module storing in a computer readable medium and/or relaying such information to the patient or to a remote computer via the mobile telephone; (I) a communication module capable of communicating with an IMD and a mobile telephone, the module, upon receiving instruction from a remote computer via the mobile telephone, interrogating the implantable device to assess operational performance of the device and/or the health status of the patient, the module relaying such information to the patient or to a remote computer via the mobile telephone; (j) a communication module capable of communicating with an IMD and a mobile telephone, the module, upon receiving instruction from a remote computer via the mobile telephone, relaying information stored in a computer readable storage medium contained within or attached to the module, where the information concerns performance of the IMD or the module, and/or the health status of the patient, to the patient and/or the remote computer via the mobile telephone; (k) use of a robust web-based remote expert data center, remote computer system or remote health care provider or health care provider, preferably accessible worldwide, to manage and tune software relating to the operational and functional parameters of the communication module or the IMD, most preferably in real-time or near real-time; (l) remote diagnosis, analysis, maintenance, upgrade, performance tracking, tuning and adjustment of a communication module or IMD from a remote location; (m) use of a highly flexible and adaptable communications scheme to promote continuous and preferably real-time data communications between a remote expert data center, remote computer, and/or remote health care provider or health care provider and the communication module via a mobile telephone; (n) a communications system capable of detecting whether a component or software defect exists in the IMD and/or the communication module; (o) a communications system wherein if a defect or fault is discovered, the system is capable of determining whether a remote "fix" is possible—if not, the system broadcasts an alert to a remote health care provider, remote computer or remote expert based computer system, most preferably attending to the problem on a real-time basis; (p) a communications system capable of performing, by way of example only, data base integrity checks, mean time between failure status of predetermined components and their associated embedded systems; (q) a communications system capable of mining patient history, performance parameter integrity and software status from the communication module, (r) an automatic medical service invoicing or billing system, and (s) methods and processes associated with all the foregoing devices and/or systems.

One embodiment of the present invention relates generally to a communications scheme in which a remote computer or computer system, or a remote health care provider, communicates with an IMD implanted within a patient by communicating through a mobile telephone and/or PDA and a communication module located near the patient, where the communication module is operatively connected to the mobile telephone and/or PDA and is capable of telemetrically uploading and downloading information to and from the IMD, and thence via the mobile telephone or PDA to the remote computer or health care provider. In some embodiments of the present invention, communications between the remote computer system or remote health care provider and the IMD include remotely debugging, updating or installing new software in the IMD or the communication module.

Another embodiment of the present invention comprises a communication module linked or connected via a mobile telephone to a remote health care provider or remote computer through the now nearly global mobile telephone communications network (which here is defined to include the Internet). At one end of the operative structure there is a remote computer, a remote web-based expert data center, and/or a remote health care provider. At the other end of the operative structure lies a mobile telephone or PDA operatively connected to a communication module, where the communication module is in turn capable of communicating with the IMD and is optionally capable of storing information obtained from the IMD therein. In-between the two foregoing ends of the system of that embodiment lies the worldwide telephone/Internet communications system.

In yet another embodiment of the present invention, the critical components, embedded systems of and software in the communication module and/or the IMD may be remotely maintained, debugged and/or evaluated via the mobile telephone and/or PDA to ensure proper functionality and performance by down-linking suitable software or diagnostic routines or instructions originating at the remote computer, the remote health care provider, or the remote web-based expert data center, or by up-linking software loaded into the communication module and/or IMD for comparison or evaluation by the remote computer, the remote health care provider, or the remote web-based expert data center. The operational and functional software of the embedded systems in the IMD and/or the communication module may be remotely adjusted, upgraded or changed as required. At least some software changes may be implemented in the IMD by downlinking from the communication module to the IMD.

In some embodiments of the present invention, the performance of the IMD, or physiologic signals or data indicative of the patient's health status, may be remotely monitored or assessed by the remote health care provider, the remote computer or computer system, or the remote expert data center via the mobile telephone and/or PDA and the communication module.

In other embodiments of the present invention, there are provided communications systems comprising integrated and efficient methods and structures for clinical information management in which various networks, such as by way of example only, Local Area Networks (LANs), Wide Area Network (WANs), Integrated Services Digital Network (ISDNs), Public Switched telephone Networks (PSTNs), the Internet, wireless networks, asynchronous transfer mode (ATM) networks, satellites, mobile telephones and other networks are implemented and coordinated with one another to transfer information to and from the IMD through the communication module and the mobile telephone to a remote computer, remote computer system, remote expert network, and/or a remote health care provider or other authorized user.

In the interest of brevity and simplicity, the applicants refer to the various foregoing and other communications system as "communications systems." It is to be noted, however, that such communication systems are interchangeable in the context of the present invention and may relate to various types of cable, fiber optic, microwave, radio, laser and other communication systems, or any practical combinations thereof.

The present invention provides significant compatibility and scalability in respect of web-based applications such as telemedicine and emerging web-based technologies such as tele-immersion. For example, the system may be adapted to applications in which a mobile telephone uplinks to a remote data center, remote computer, remote computer system or remote health care provider or authorized user via a mobile telephone to transfer data stored in the communication module or obtained from the IMD, or to receive data from such remote computers or health care providers. In these and other applications, the data so transferred or received may be employed as a preliminary screening tool to identify the need for further intervention or action using web technology.

BRIEF DESCRIPTION OF THE DRAWINGS

The present invention will become better understood by reference to the following Detailed Description of the Preferred Embodiments of the present invention when considered in connection with the accompanying Figures, in which like numbers designate like parts throughout, and where:

FIGS. 6A through 6C show simplified schematic and flow diagrams of various embodiments of the principal communications components of the present invention;

FIGS. 11A and 11B show flow charts for two methods of the present invention relating to remote system 130 and/or remote health care provider 136 initiated communication between IMD 10 and/or communication module 100 and/or mobile telephone or PDA 110 and various components of remote system 130 via communication system 120;

DETAILED DESCRIPTION OF THE PREFERRED EMBODIMENTS

Figure 1:
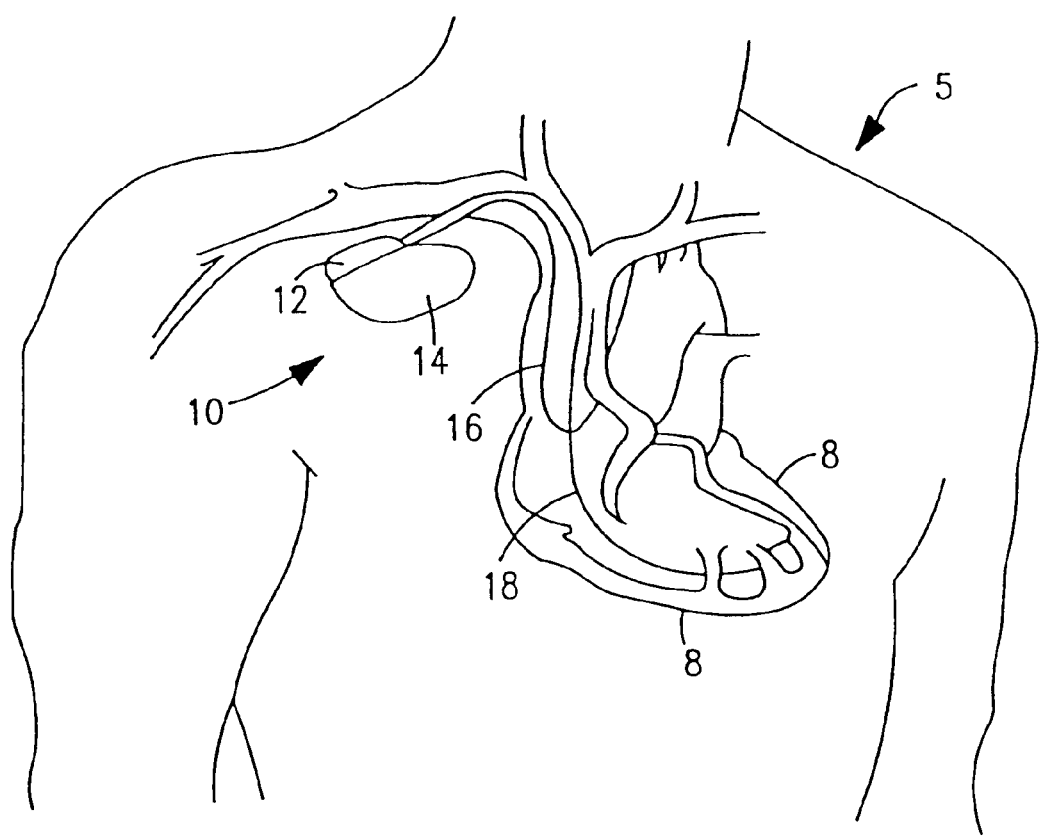
FIG. 1 shows a simplified schematic view of one embodiment of an IMD that may be employed in conjunction with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
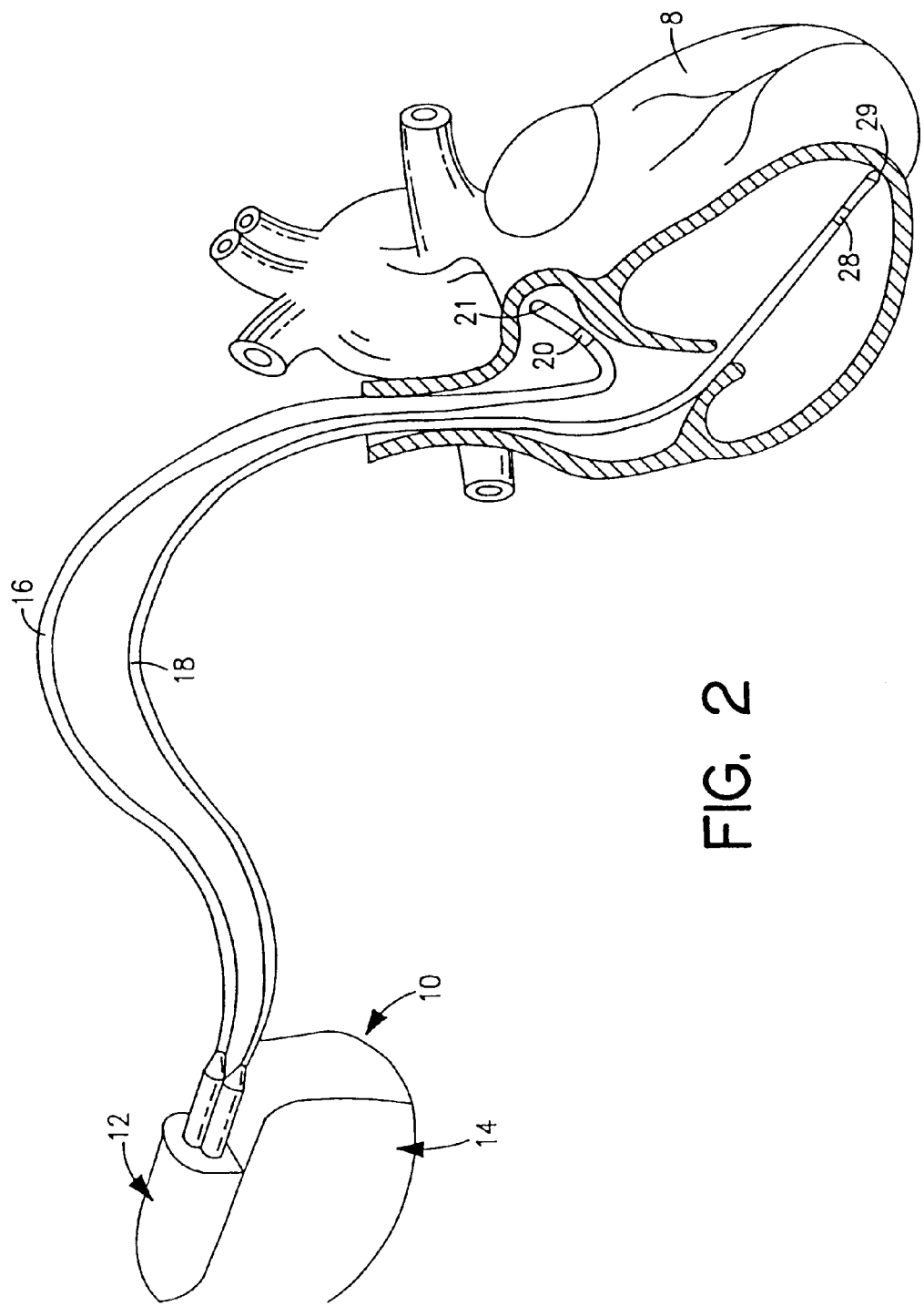
FIG. 2 shows a simplified illustration of an IMD with medical electrical leads positioned within passageways of a heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
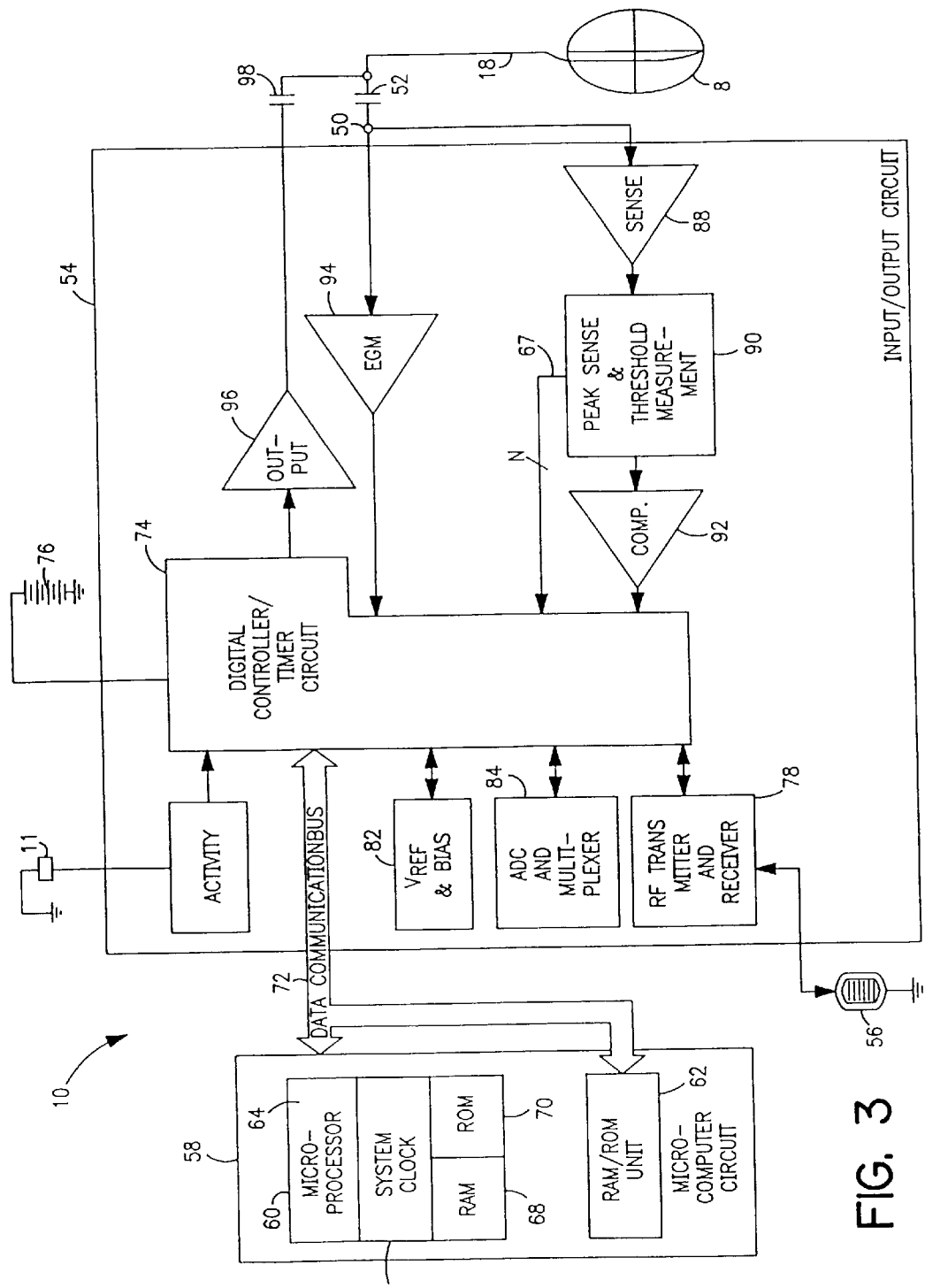
FIG. 3 shows a block diagram illustrating some constituent components of an IMD.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of both an external programming unit (not shown in the Figures) and communication module 100, more about which we say later. One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple- chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
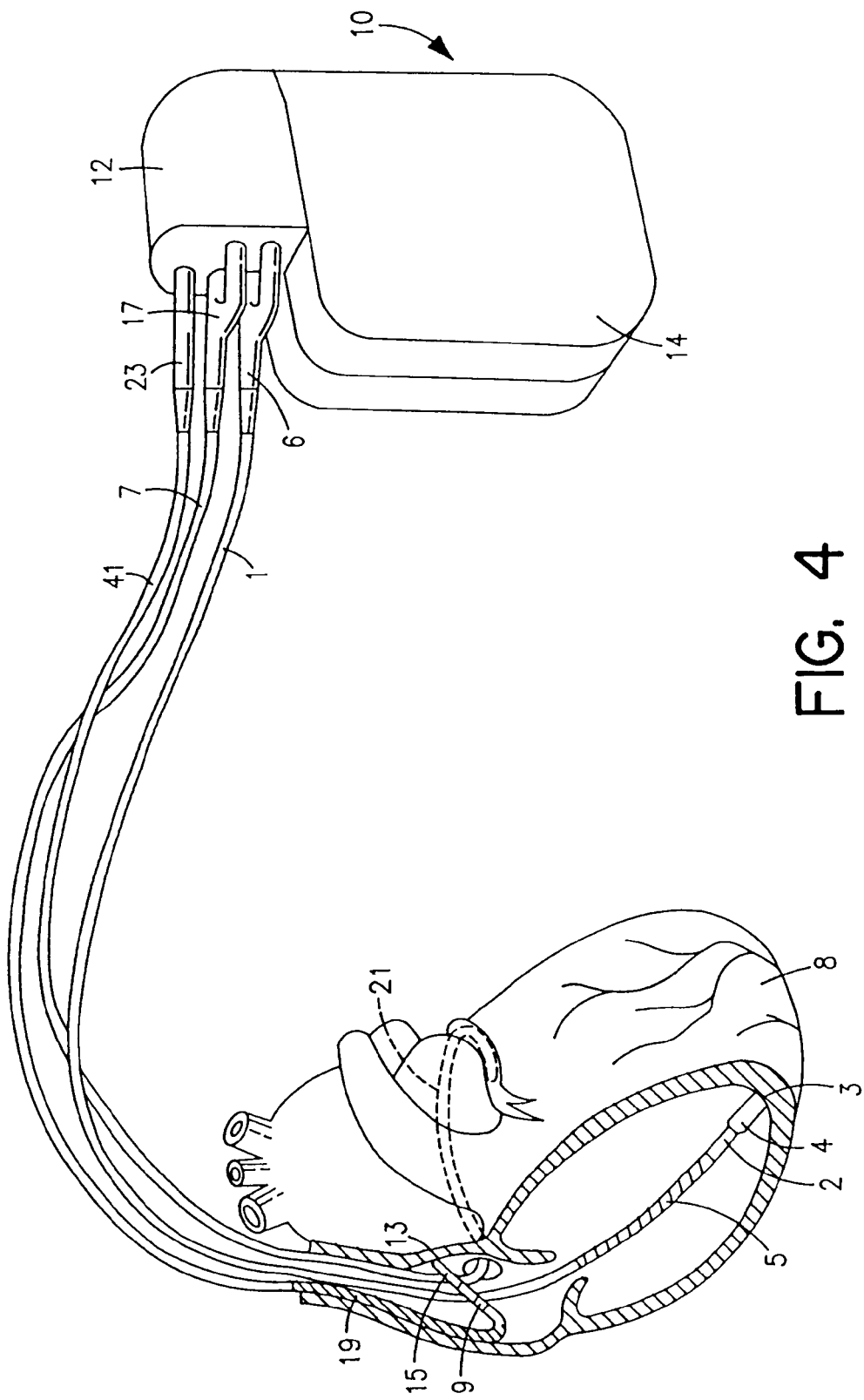
FIG. 4 shows a simplified schematic view of an IMD with medical electrical leads positioned within passageways of a heart.
Figure 5:
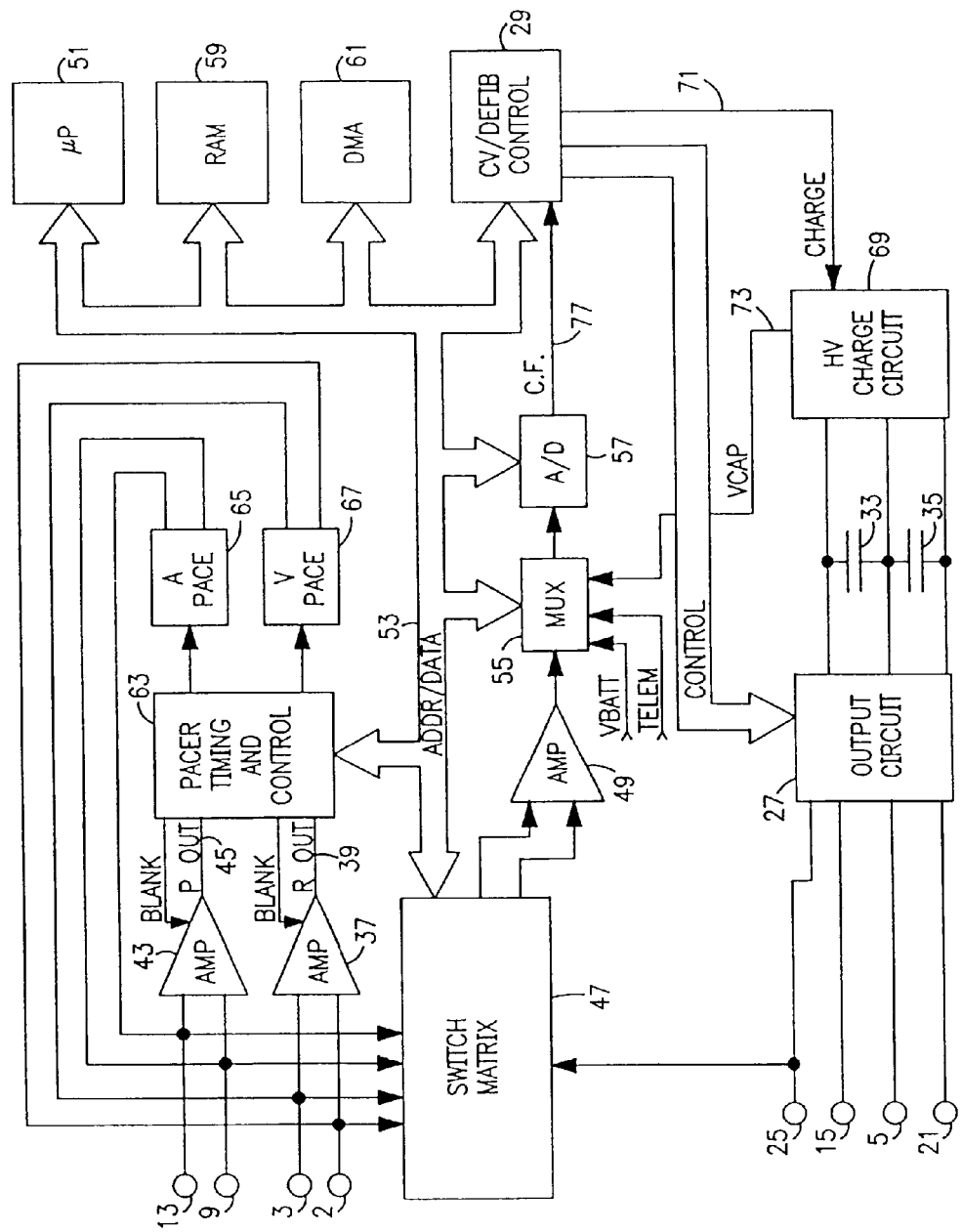
FIG. 5 shows a partial block diagram illustrating one embodiment of an IMD that may be employed in conjunction with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by AID converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known in the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known in the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R–R intervals, P–P intervals, P–R intervals and R–P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R–R or P–P intervals of an average rate indicative of tachyarrhythmia or an unbroken series of short R–R or P–P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be any type of implantable medical device, including, but not limited to, an implantable nerve stimulator or muscle stimulator such as those disclosed in U.S. Pat. No. 5,199,428 to Obel et al., U.S. Pat. No. 5,207,218 to Carpentier et al. and U.S. Pat. No. 5,330,507 to Schwartz, an implantable monitoring device such as that disclosed in U.S. Pat. No. 5,331,966 issued to Bennet et al., an implantable brain stimulator, an implantable gastric system stimulator, an implantable vagus nerve stimulator, an implantable lower colon stimulator (e.g., in graciloplasty applications), an implantable drug or beneficial agent dispenser or pump, an implantable cardiac signal loop or other type of recorder or monitor, an implantable gene therapy delivery device, an implantable incontinence prevention or monitoring device, an implantable insulin pump or monitoring device, and so on. Thus, the present invention is believed to find wide application in conjunction with almost any appropriately adapted implantable medical device.

Figure 6A:
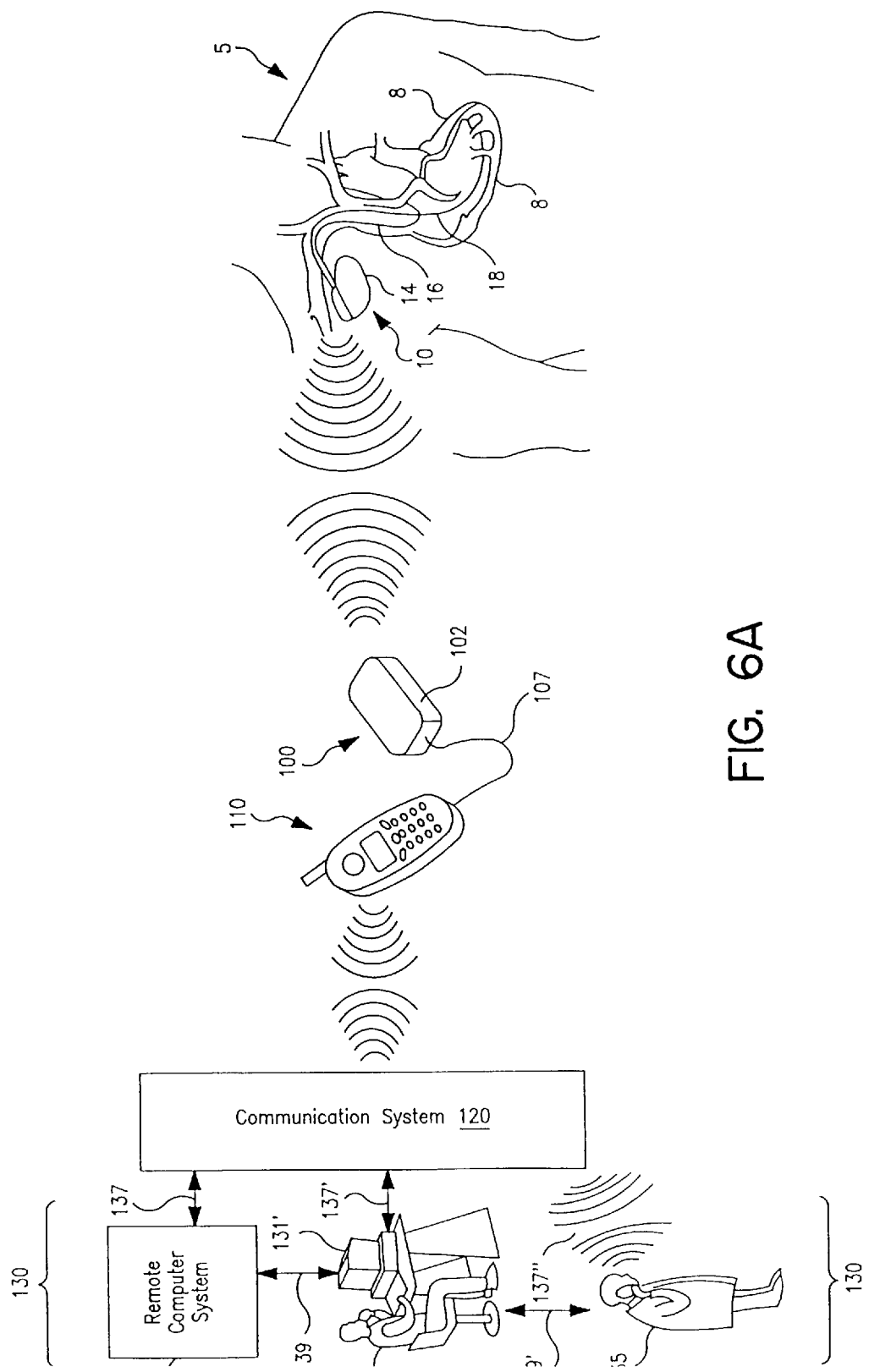
Figure 6C:
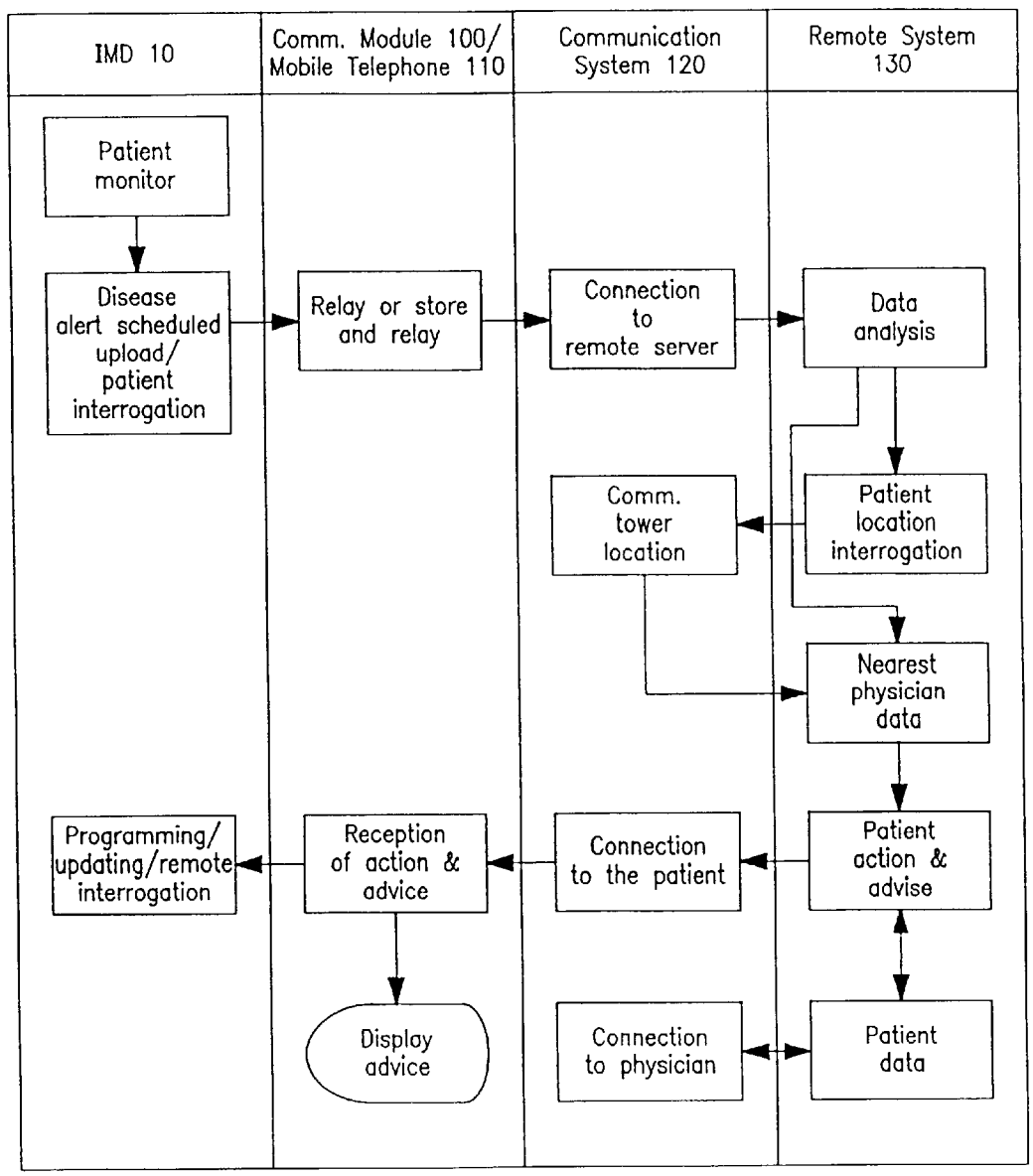

FIGS. 6A, 6B and 6C show simplified schematic and flow diagrams of various embodiments of the principal communications components of the present invention. It is to be understood that the term "remote system" employed in the specification and claims hereof includes within its scope the terms "remote computer", "remote computer system", "remote computer network", "remote expert data center", "remote data resource system", "data resource system", and like terms. It is further to be noted that the term "remote health care provider" employed in the specification and claims hereof includes within its scope the terms "physician", "field clinical engineering representative", "remote authorized user", "operator", "remote user", "database specialist," "clinical specialist," "nurse," "computer specialist", "remote operator", "remote user" and like terms, and that the term "remote system" encompasses the foregoing terms.

Figure 7:
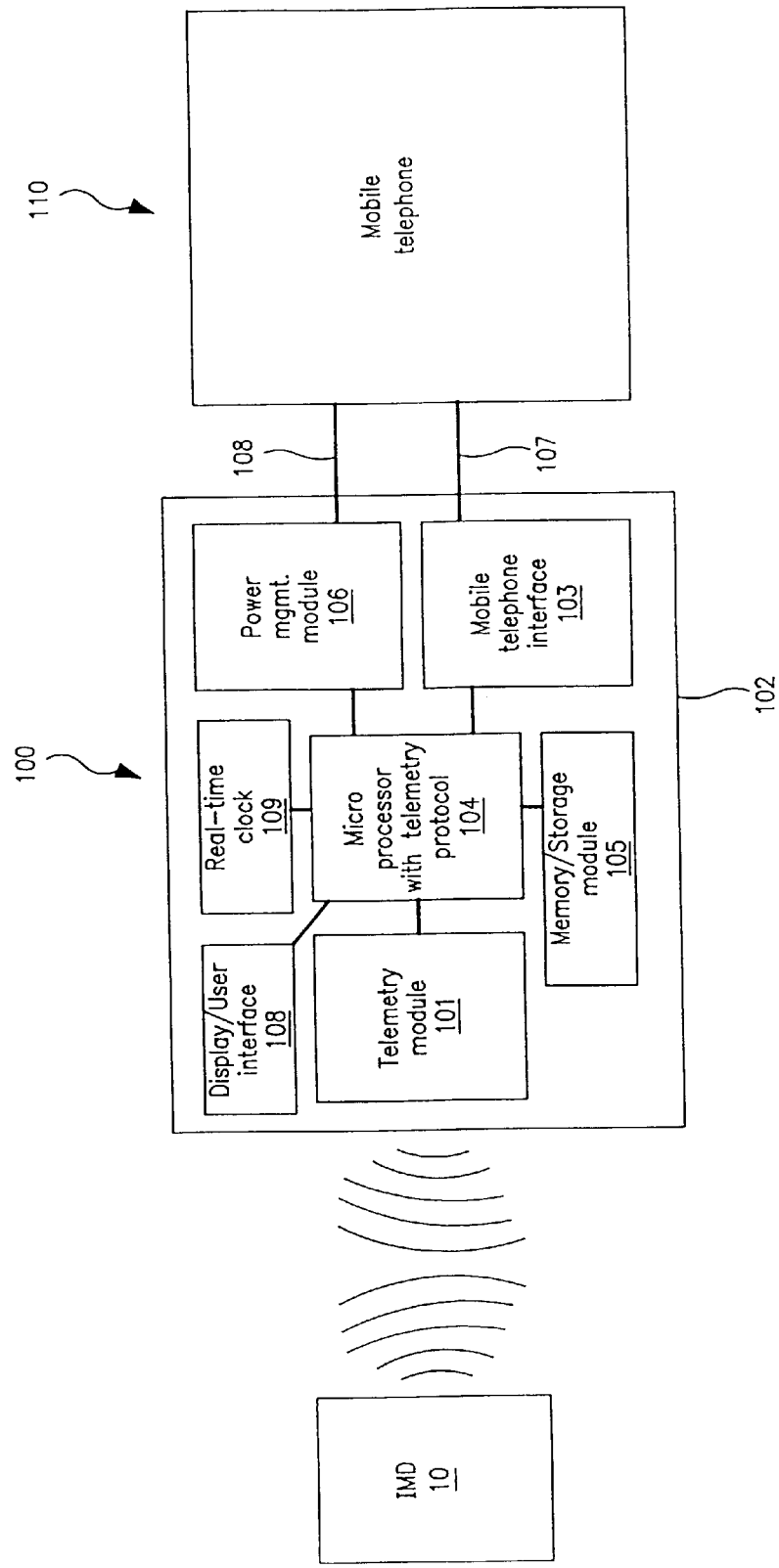
FIG. 7 shows a block diagram illustrating major components of one embodiment of a communication module of the present invention.

Referring now to FIGS. 6A and 7, there is shown a simplified schematic diagram of the major components of the present invention comprising IMD 10, communication module 100, mobile telephone 110, telephone/Internet communications network 120, and remote computer or remote health care provider 130. In the embodiment of the present invention illustrated in FIGS. 6A and 8, communication module 100 is disposed within housing 102 and is connected by a suitable interface to mobile telephone 110 via link, connection, cable or line 107. Hardwired link, connection, cable or line 107 may be replaced with a wireless link, as discussed in further detail below. Via link 107 or other suitable means, mobile telephone 110 receives information or data from, or sends information or data to, communication module 100. IMD 10 receives information or data from, or sends information or data to, communication module 100, most preferably via RF telemetric means discussed in further detail below. Thus, communication module 100 acts as a go-between in respect of mobile telephone 100 and IMD 10. In some embodiments of the present invention, communication module 100 and mobile telephone supplant, eliminate or reduce the requirement for a conventional implantable medical device programmer such as a MEDTRONIC 9790 Programmer to communicate with IMD 10.

The hardware and/or software of communication module 100 may be configured to operate in conjunction with a plurality of different implantable medical devices 10. The particular type of IMD 10 to be communicated with may be pre-programmed in module 100, or may be selected before or at the time IMD is to be communicated with. For example, communication module 10 may be selectably configured or pre-programmed or configured to communicate with, receive data from, and/or download data to any of the various commercially available IMDs manufactured and sold by MEDTRONIC, BIOTRONIK, CARDIAC PACEMAKERS, GUIDANT, ELA, SIEMENS, SORIN, NEUROCOR, ADVANCED NEUROLOGICAL SYSTEMS, CYBERONICS and/or TERUMO using telemetry communication protocols and techniques well known in the art.

Communication system 120 includes within its scope the existing worldwide telephone and Internet communications network, as well as future embodiments thereof. Communication system 120 permits communication module 100/mobile telephone or PDA 110 to communicate with remote system 130 via communication system 120.

Remote system 130 may comprise any one or more of remote computer system 130, remote computer system 131', remote health care provider, physician, database specialist, clinical specialist, nurse, computer specialist and/or operator 136, and/or remote physician 135. In addition to being capable of communicating with communication module 100/mobile telephone or PDA 110 via communication system 120, remote computer system 131 may communicate with directly with computer system 131' and/or remote health care provider, physician, database specialist, clinical specialist, nurse, computer specialist and/or operator 136 through link 139, or through links 137 and 137' via communication system 120.

Remote computer system 131 may also be configured to communicate directly with physician 135, or to communicate with physician 135 via links 137 and 137" through communication system 120. Computer system 131' and/or remote health care provider, physician, database specialist, clinical specialist, nurse, computer specialist or operator 136 may also communicate with physician 130 directly through link 139', or through-links 137' and 137" via communication system 120.

It will now become clear to those skilled in the art upon considering the present disclosure that many different permutations and combinations of any pair or more of communication module 100, mobile telephone 110, communication system 120, remote computer system 131, remote computer system 131', remote health care provider, physician, database specialist, clinical specialist, nurse, computer specialist and/or operator 136, physician 135, and links 137, 137', 137", 139 and 139' are possible, all of which are intended to fall within the scope of the present invention.

FIG. 6C shows simple flow diagrams corresponding to one method of the present invention where IMD 10, communication module 100/mobile telephone or PDA 110 and remote system 130 communicate with another via communication system 120. IMD 10 may monitor various aspects of the patient's health, and store same in memory as information or data. Upon IMD 10 detecting a threshold event (e.g., detection of arrhythmia or fibrillation in patient 5) or receiving instruction from patient 5 or remote system 130, IMD may upload stored information or data to remote system 130 via communication module 100, mobile telephone 110 and communication system 130. IMD 10 may be interrogated directly by patient 5, or may be interrogated remotely by remote system 130 via communication module 100 and mobile telephone 110. The system of the present invention may also include provisions for determining the geographical location of the patient using mobile cell telephone location data or by incorporating or otherwise operably connecting a Global Positioning System (GPS) module into communication module 100 or mobile telephone 110.

In one embodiment of the present invention, IMD automatically contacts remote system 130 via communication module 100 and mobile telephone 110 in response to detecting a life-threatening or serious condition in the patient's health. In response to receiving information concerning the detected condition from IMD 10, remote system 130 may be employed to automatically or under the supervision of health care provider 135 or 136 provide an appropriate response, such as the delivery of instructions to IMD 10 to deliver a specific therapy or alerting an emergency, ambulance or paramedic service to proceed immediately to the location of patient 5. As discussed above, the patient's specific location may be provided by various means, such as GPS or mobile telephone cell location identification information.

In another embodiment of the present invention, patient 5 senses a physiologic event and is sufficiently concerned respecting same to manipulate user interface 108 to cause data already uploaded into the memory of communication module 100 (or data uploaded into the memory of communication module 100 in response to the patient's manipulation of interface 108) to be relayed to remote system 130 for analysis and further action or response. In response to receiving information concerning the patient's health status from communication module 100, remote system 130 may be employed to automatically or under the supervision of health care provider 135 or 136 provide an appropriate response, such as the delivery of instructions to IMD 10 to deliver a specific therapy or alerting an emergency, ambulance or paramedic service to proceed immediately to the location of patient 5. Once again, the patient's specific location may be provided by various means, such as GPS or mobile telephone cell location identification information.

FIG. 7 shows some basic components of communication module 100 according to one embodiment of the present invention. Communication module 100 preferably comprises microprocessor, CPU, micro-computer or controller 104 for controlling the operation of module 100 and the exchange of data and information between IMD 10 and mobile telephone 110, telemetry module 101 for communicating with IMD 10, memory/storage module 105 for storing or recalling information or data in memory, a hard disk, or another computer readable medium such as flash memory, ROM, RAM, EEPROM, and the like, power management module 106 for monitoring the state of charge and/or controlling the discharge of a battery located in mobile telephone 110 or in communication module 100, real time clock 109 for providing timing signals to computing and controlling device 104, and display and/or user interface 108.

Referring now to FIGS. 6A and 7, electronics disposed within communication module 100 are most preferably electrically powered by one or more primary or secondary (i.e., rechargeable) batteries disposed within or attached to mobile telephone 110 using line or cord 108. Communication module 100 may also be powered by such batteries disposed within housing 102, other portable energy sources, solar panels, capacitors, supercapacitors, appropriately filtered and rectified household line ac power, or any other suitable power source. Power management module 106 is preferably configured to minimize current drain from whatever battery it is that is being employed to power communication module 100 by utilizing wake-up mode and sleep mode schemes well known in the implantable medical device and mobile telephone arts. Power management module 106 may also be configured to permit communication module 100 to be powered electrically by its own internal battery or the battery of the mobile telephone in accordance with a priority scheme assigned to the use of those batteries. Thus, if one battery's state of charge becomes too low, power management module 106 may be configured to switch to the remaining battery as an electrical power source for communication module 100 and/or mobile telephone 110.

Interface 103 may be any suitable interface, such as a serial or parallel interface. Cable or line 107 may include or be combined with line or cord 108. In a preferred embodiment of the present invention, the end of line 107 that attaches to mobile telephone 110 comprises a standardized connector which plugs directly into a corresponding standardized or manufacturer-specific connectors for such as the connectors found in many off-the-shelf, unmodified, commercially-available mobile telephones or PDAs. In another embodiment of the present invention, and as discussed in further detail below, communication module 100 and mobile telephone 110 communicate wirelessly by, for example, RF, optical or infrared means and are not physically connected to one another.

As shown in FIG. 6B, communication module 100 may be incorporated into or attached directly to the housing of mobile telephone 110. In one such embodiment of the present invention, at least portions of the exterior housing of an off-the-shelf mobile telephone, PDA and/or combined mobile telphone/PDA are modified to permit communication module 100 to be integrated into mobile telephone or PDA 110 such that mobile telephone or PDA 110 and communication module 100 form a single physical unit, thereby lending increased portability to the communication module of the present invention. Communication module 100 and mobile telephone or PDA 110 may also be configured and shaped such that module 100 clips onto or otherwise attaches to mobile telephone 110 in a detachable, semi-permanent or other manner. Although not shown explicitly in FIG. 6B or the other Figures, in the present invention it is of course contemplated that mobile telephone or PDA 110 communicate with remote system 130 via communication system 120, where communication system 120 most preferably includes towers, transmitter, dishes, fiber optic cables, conventional hard wiring, RF links, transponders and other reception and transmission devices capable-of relaying or transponding signals received from or sent to mobile phone or PDA 110.

In still another embodiment of the present invention, an off-the-shelf mobile telephone or PDA 110 may be modified such that only a limited number of buttons having predetermined functions are presented to and available for patient 5 to push. For example, such a modified mobile telephone could present patient 5 with one or more of "emergency 911 alert", "acquire IMD status", "acquire patient health status", or "contact health care provider" buttons, which when pressed will thereafter automatically execute the indicated instruction. Other buttons might not be provided on such a modified mobile telephone to avoid confusing patient 5. Similarly, such a limited number of buttons having predetermined functions could be incorporated into communication module 100, into combined mobile telephone 110/communication module 100, or into a mobile telephone adapted for use by physician 135 or remote health care provider 136 in the system of the present invention.

As shown in FIG. 7, communication module 100 may include optional display and/or user interface 108 for conveying certain information to or from patient 5. Such information may include, without limitation, the current performance status of IMD 10, the patient's current health status, confirmation that an operation is being carried out or has been executed by module 100 or mobile telephone 110, indication that a health care provider is attempting to communicate or is communicating with patient 5, communication module 100 or IMD, indication that successful telemetry communication between IMD 10 and module 100 is in progress, and the like. Display and/or user interface 108 may comprise, by way of example only, one or more LEDs, an LCD, a CRT, a plasma screen, any other suitable display device known in the mobile telephone, implantable medical device, computer, consumer appliance, consumer-product or other arts. Display and/or user interface 108 may also comprise, by way of example only, a keyboard, push-buttons, a touch panel, a touch screen, or any other suitable user interface mechanism known in the mobile telephone, implantable medical device, computer, consumer appliance, consumer product or other arts.

Referring now to FIGS. 6A and 7, communication module 100 preferably communicates with mobile telephone 110 via mobile telephone interface 103 and line or connection 107 using standardized serial communication protocols and hardware and/or software controlled handshakes associated with RS-232 connectors (although other communication protocols and handshakes may certainly be employed in the present invention, including those which utilize parallel communication interfaces). Interface 103 may comprise a PCMCIA (Personal Computer Memory Card International Association) modem card interface for communication between communication module 100 and mobile telephone 110. For example, interface 103 may comprise a standard PCMCIA plug-and-play 56 kbaud modem card adapted to be connected to mobile telephone 110 using a serial or parallel connecting cable of the type well known in the mobile telephone and computer arts.

Communication module 100 may also be adapted to receive other types of PCMCIA cards, such as data storage cards and data memory cards for memory/storage module 105, display cards for display 108, and so on. PCMCIA cards suitable for use in various embodiments of the present invention may be PCMCIA Type I cards up to 3.3 mm thick (used primarily for adding additional ROM or RAM to a communication module 100), PCMCIA Type II cards up to 5.5 mm thick (used primarily for modem and fax modem cards), and PCMCIA Type III cards up to 10.5 mm thick (sufficiently large for portable disk drives). Various types of PCMCIA slots may also be disposed in communication module 100 to receive the foregoing PCMCIA cards, including Type I slots, Type II slots, and Type III slots.

In another embodiment of the present invention, communication module 100 and mobile telephone 110 may not be physically connected to one another by a data line or cord 107, and instead communicate wirelessly through, by way of example only, RF or infrared means. Likewise, antenna or coil 101 may be separate or detachable from communication module and be capable of communicating wirelessly with communication module 100.

Wireless communication between at least some components of the communication system of the present invention located near, on or in patient 5 may be accomplished or assisted using devices which conform to the BLUETOOTH standard, a 2.4 GHz wireless technology employed to transport data between cellular phones, notebook PCs, and other handheld or portable electronic gear at speeds of up to 1 megabit per second. The BLUETOOTH standard was developed by the Bluetooth Special Interest Group (or "BSIG"), a consortium formed by Ericsson, IBM, Intel, Nokia and Toshiba. The BLUETOOTH standard is designed to be broadband compatible, and capable of simultaneously supporting multiple information sets and architecture, transmitting data at relatively high speeds, and providing data, sound and video services on demand. Of course, other suitable wireless communication standards and methods now existing or developed in future are contemplated in the present invention. It is to be noted that under some circumstances difficulty will be encountered employing BLUETOOTH technology for communication with implantable medical devices owing to the relatively high power requirements of the system. Additionally, in the present invention it is contemplated that various embodiments operate in conjunction with a BLUETOOTH or BLUETOOTH-like wireless communication standard, protocol or system where a frequency other than 2.4 GHz is employed, or where infra-red, optical or other communication means are employed in at least portions of the systems of the present invention and/or in conjunction with BLUETOOTH or BLUETOOTH-like wireless RF communication techniques.

One embodiment of the present invention using the BLUETOOTH standard incorporates an RF device, a baseband controller, and flash memory. One example of an RF BLUETOOTH device finding application in the present invention is the TEMIC SEMICONDUCTOR T2901 chip which enables wireless data to be transferred at distances of 10 meters, operates in the 2.4-GHz frequency band, and has a power output of 0 dBm. The baseband controller may be a single-chip device that performs link-management and control functions, and based on an ARM 7TDMI, a 32-bit RISC-chip core from ARM, LTD.

Figure 8:
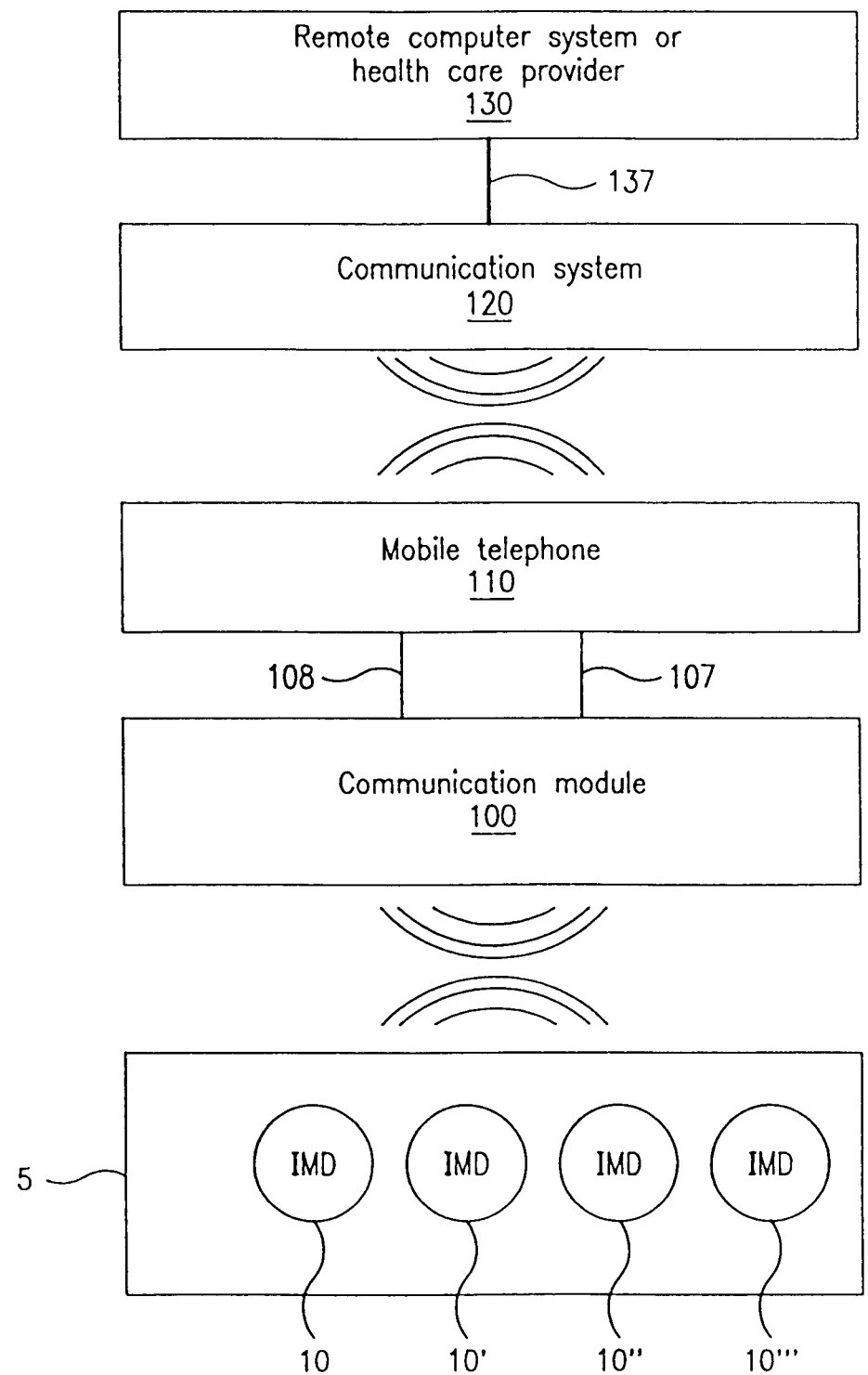
FIG. 8 illustrates various portions of a communications system in accordance with one embodiment of the present invention.

In one embodiment of the present invention, a plurality of IMDs 10 may be implanted in patient 5 (see, for example, FIG. 8). It is preferred that those IMDs be capable of capable of communicating with one another and/or with communication module 100 using, for example, conventional RF telemetry means, BLUETOOTH technology, or using so-called "Body Bus" or "Body Wave" technology. See, for example, U.S. patent application Ser. No. 09/218,946 to Ryan et al. for "Telemetry for Implantable Devices Using the Body as an Antenna" (approximately 3 MHz communication); U.S. Pat. No. 5,113,859 to Funke et al. entitled "Acoustic Body Bus Medical Device Communication System"; and U.S. Pat. No. 4,987,897 to Funke et al. entitled "Body Bus Medical Device Communication System". Each of the foregoing patents and patent application is hereby incorporated by reference herein, each in its respective entirety.

Communication module 100 and microprocessor 104 may further operate under a Microsoft Pocket PC, Windows 95, Windows 98, Windows 2000, Windows CE, LINUX, UNIX, MAC, PalmOS, EPOC, EPOC16, EPOC32, FLEXOS, OS/9, JavaOS, SYMBIAN or other suitable computer operating environment. Communication module 100 is further preferably configured to accept interchangeable plug-and-play cards therein. For example, communication module 100 may be configured to accept different plug-and-play cards for telemetry module 101, where each plug-and-play card is particularly adapted to permit telemetry module 101 to communicate in an optimal fashion with a particular type or model of IMD 10 implanted within patient 5. Thus, and by way of example only, one type of plug-and-play card may be configured to communicate particularly well with a certain model or range of models of a pacemaker, while other types of plug-and-play cards may be configured especially to communicate with nerve stimulators, drug pumps or dispensers, gastric stimulators, PCDs, ICDs, and the like.

Reference is made to U.S. Pat. No. 5,701,894 to Cherry et al. for a "Modular Physiological Computer-Recorder", hereby incorporated by reference herein in its entirety, where interchangeable plug and play signal input conditioner cards are employed in conjunction with a microprocessor system with analyzing software, and where a removable memory module for data storage is provided. Some concepts disclosed in the '894 patent to Cherry, such as interchangeable plug-and-play cards and removable memory modules, are adaptable for use in conjunction with certain portions the present invention, such as communication module 100 and microprocessor 104, memory/storage module 105, telemetry module 101, and the foregoing plug and play and/or PCM-CIA cards that may be associated therewith.

It is preferred that information, programming commands and/or data be transmitted to IMD 10 by communication module 100, and that information and data be received by communication module 100 from IMD 10, using standard RF telemetry protocols and means well known in the art of implantable medical devices. For example, MEDTRONIC Telemetry A, B or C RF communication standards may be employed to effect communications between IMD 10 and communication module 100, and/or between IMD 10 and other IMDs implanted within patient 5. Alternatively, communication methods described in the foregoing '859 and '897 patents to Funke and the '946 patent application to Ryan et al. may be employed to effect communications between IMD 10 and communication module 100, and/or between IMD 10 and other IMDs implanted within patient 5.

According to Telemetry A, B or C RF communication standards, RF communication occurs at frequencies of about 175 kHz, about 175 kHz and about 400 MHz, respectively, with respective communication ranges between IMD 10 and communication module 100 of about 1" to about 4", about 1" to about 4", and about 1" and about 20 feet. Communication module 100 thus preferably comprises a telemetry antenna or coil 101, which may be an externally detachable RF head or equivalent well known in the art, or which may be incorporated within housing 102. It is preferred that communication module 100 be operative when placed within a few feet of patient 5 so that module 100 may communicate with IMD 10 when patient 5, for example, is undergoing a treadmill test. Communication module 100 is preferably configured to permit communication according to the Telemetry A, B and C communication standards so that communication with a wide range of old, new and future models and types of IMDs is possible.

Referring now to FIGS. 3, 6A and 7, antenna 56 of IMD 10 is connected to input/output circuit 54 to permit uplink/downlink telemetry through RF transmitter and receiver telemetry unit 78. Information and/or data are exchanged between IMD 10 and communication module 100 by means of an antenna or coil forming a part of telemetry module 101 in communication module 100 and antenna 56 disposed in IMD 10. Telemetry module 101 may feature a detachable RF head comprising a coil or antenna of the type well known in the implantable medical device arts. Alternatively, the coil or antenna of telemetry module 100 may be incorporated into communication module 100 such that module 100 is contained within a single housing, or within the housing of mobile telephone 110.

Telemetry module 101 preferably comprises an external RF telemetry antenna coupled to a telemetry transceiver and antenna driver circuit board which includes a telemetry transmitter and telemetry receiver. The telemetry transmitter and telemetry receiver are preferably coupled to control circuitry and registers operated under the control of computing and control device 104. Similarly, within IMD 10, RF telemetry antenna 56 is coupled to a telemetry transceiver comprising RF telemetry transmitter and receiver circuit 78. Circuit 78 in IMD 10 is coupled to control circuitry and registers operated under the control of microcomputer circuit 58.

According to one embodiment of the present invention, telemetry coil or antenna 101 may be incorporated into a belt, harness, strap, bandage, or article of clothing which the patient wears and that positions coil or antenna of telemetry module 101 directly over or otherwise in close proximity to the patient's heart 8 to thereby provide suitable RF coupling between IMD 10 and communication module 100. In such an embodiment of the present invention, communication module 100 may be attached to patient 5 along with mobile telephone 110 using, by way of example only, a belt or fanny pack, while coil or antenna of telemetry module 101 is attached to module 100 using a suitable wire or cord, thereby permitting the patient considerable freedom of movement. See, for example, Provisional U.S. patent appln. Ser. No. 60/197,753 for "ECG and RF Apparatus for Medical Device Systems" filed Apr. 19, 2000 and corresponding U.S. patent application Ser. No. 09/696,319 filed Oct. 25, 2000 for "Method and Apparatus for Communicating with Medical Device Systems" to Pool et al., the respective entireties of which are hereby incorporated by reference herein.

As discussed above, uplinking of IMD 10 to, or downlinking to IMD 10 from, remote system 130 may be effected through mobile telephone or PDA 110 and telephone/Internet communications network or communication system 120. Accordingly, communication module 100, mobile telephone 110 and communication system 120 function as an interface between IMD 10 and remote computer system 130.

Communication module 100 may also be configured to permit a dual uplinking capability, where module 100 is capable of uplinking data and/or information both to mobile telephone 110 and to a standard implantable medical device programmer (not shown in the Figures), such as a MEDTRONIC 9790 Programmer or a programmer of the type disclosed in U.S. Pat. No. 5,345,362 to Winkler, hereby incorporated by reference herein in its entirety. Thus, in such an embodiment of the present invention, IMD 10 may be communicated with remotely in accordance with the methods and devices of the present invention, or may be communicated with conventional fashion, according to the patient's and health care provider's needs at any particular time.

One feature of the present invention is the use of various scalable, reliable and high-speed wireless or other communication systems in communication system 120 to bi-directionally transmit high fidelity digital and/or analog data between communication module 100 and remote system 130. A variety of wireless and other suitable transmission and reception systems and combinations thereof may be employed to help establish data communications between communication module 100 and remote system 130, such as, without limitation, stationary microwave antennas, fiber optic cables, conventional above-ground and underground telephone cables and RF antennas well known in the art of mobile telephony.

As discussed above, remote system 130 and communication module 100 are linked by mobile telephone 110 and communication system 120. In one embodiment of the present invention, communication system 120 comprises a GSM network system comprising a mobile station carried by the patient, a base station subsystem for controlling the radio link with the mobile station, and a network subsystem (the main part of which is a mobile services switching center which performs the switching of calls between the mobile and other fixed or mobile network users, as well as management of mobile services, such as authentication), and an operations and maintenance center which oversees the proper operation and setup of the network. The GSM mobile station and the base station subsystem communicate across an air interface or radio link. The base station subsystem communicates with the mobile service switching center across another interface.

Examples of telephone, computer and mobile telephone communication air interface standards, protocols and communication systems that may be employed in conjunction with communication module 100, mobile telephone 110, communication system 120, and remote system 130 of the present invention include, but are in no way limited to the following:

ATM;

AXE;

AMPS (Advanced Mobile Phone Service);

CDMA (Code Division Multiple Access);

DECT (Digital Enhanced Cordless Telecommunication);

Dual-mode combined mobile satellite and cellular standards (employed by such Mobile Satellite Services (MSSs) such as Immarsat, Odyssey, Globalstar, Teledesic, ICO, Thuyra, ACes, Agrani, EAST and the now defunct Iridium system).

GSM (Geostationary Satellite Standard);

GMSS (Geostationary Mobile Satellite Standard);

GPRS (General Packet Radio Service—a standard for wireless communications which runs at speeds up to 150 kilobits per second, compared with current GSM systems' 9.6 kilobits per second—which supports a wide range of bandwidths and is particularly suited for sending and receiving small bursts of data, such as e-mail and Web browsing, as well as large volumes of data; see, for example, Japan's NTT DoCoMo I-mode system);

IMEI (International Mobile Equipment Identity—a unique number given to every mobile phone and stored in a database—the EIR or Equipment Identity Register—containing all valid mobile phone equipment; when a phone is reported stolen or is not type approved, the number is marked invalid);

I-Mode (Japanese NTT DoCoMo Inc. system and protocol for permitting internet access via mobile telephones)

IP Telephony Standards and communication systems; and

MOBITEX Virtual Private Networking;

MOEBIUS (Mobile Extranet Based Integrated User Service);

NMT (Nordic Mobile Telephony);

PCS (Personal Communications Services);

PDA (Personal Data Assistant, e.g., PALM and PALM-type "computing platforms" and/or "connected organizers");

PDC (Personal Digital Cellular);

Signaling System 7 (a telecommunications protocol defined by the International Telecommunication Union—ITU—as a way to offload PSTN data traffic congestion onto a wireless or wireline digital broadband network);

SIM (Subscriber Identity Module—smart cards that fit into GSM handsets, holding information on the phone subscriber and GSM encryption keys for security SIM cards that allow GSM subscribers to roam in other GSM operator networks);

SIM Toolkit (a GSM standard adopted in 1996 for programming a SIM card with applications—the SIM toolkit allows operators to offer new services to the handset);

SMS (Short Message Service, or the transmission of short text messages to and from a mobile phone, fax machine and/or IP address—messages must be no longer than 160 alpha-numeric characters and contain no images or graphics);

SMSC (Short Message Service Center—used in conjunction with SMS to receive short messages);

TACS (Total Access Communication System);

TDMA (IS-136 specification for advanced digital wireless services);

3G (Third Generation of digital wireless technology, promising to bring data speeds of between 64,000 bits per second to 2 megabits per second—this next generation of networks will generally allow downloading of video, high quality music and other multimedia—the phones and networks also promise to offer cellular phone customers worldwide roaming capabilities because all 3G handsets are expected to contain a universal SIM);

UMTS (Universal Mobile Telecommunications System or Third Generation (3G) mobile technology capable of delivering broadband information at speeds up to 2 Mbit s/sec, and in addition to voice and data, delivering audio and video to wireless devices anywhere in the world through fixed, wireless and satellite systems);

WAP (Wireless Application Protocol);

WCDMA (Wideband Code Division Multiple Access), and

WCDMA (Wideband Code Division Multiple Access);

In the present invention, it is preferred that communication system 120 offer a combination of all-digital transparent voice, data, fax and paging services, and that system 120 further provide interoperability between mobile satellite and cellular networks. It is also preferred in the present invention that communication system 120 permit patients to use mobile phones that are compatible with satellite systems in any country as well as across a plurality of geographic regions, thereby creating roaming capabilities between different systems' regional footprints. In one such embodiment of the present invention, mobile telephone 110 may be , for example, a Motorola P7389 tri-band mobile telephone or similar device, or include a universal SIM, WAP or other card, chip or code designed to allow patient 5 or health care provider 136 worldwide roaming privileges.

Smart features or cards may be incorporated into mobile phone 110 to offer increased security for Internet, international and other transactions or communications. Moreover, mobile phone 110 may be a "dual-slot" phone having a second slot or connector into which patient 5 or health care provider 136 can insert a chip-based card or module for medical service payments, applications, programming, controlling, and/or assisting in controlling the operation of mobile phone 110 and/or communications module 100. Mobile phone 110 may also be configured to accept PCM/ CIA cards specially configured to fulfill the role of communication module 100 of the present invention. Alternatively, mobile phone 110 and/or communication module 100 may receive medical service payment, application programming, controlling and/or other information or data by wireless means (e.g., BLUETOOTH technology, infrared signals, optical signals, etc.) from a chip-based card, module or sensor located in relatively close proximity to communication module 100 and/or mobile telephone 110 and in the possession of patient 5 and/or health care provider 136 or located in sufficiently close proximity to patient 5 or remote health are provider 136 so as to permit reliable communication. Mobile phone 110 may also be an off-the-shelf or specially configured phone having a plurality sensing electrodes disposed on its backside for sensing ECGs. See for example, the VITAPHONE product manufactured by vitaphone GmbH of Altrip, Germany, which product may be modified advantageously in accordance with several embodiments of the present invention upon reading the present disclosure and reviewing the drawings hereof.

In still another embodiment of the present invention, a chip-based card or module capable of effecting telemetric communications between IMD 10 and mobile phone 110 is configured for insertion into a second slot of a dual-slot phone, thereby eliminating the need to modify the housing or other portions of an off-the-shelf mobile phone 110 for use in the system of the present invention while also preserving the first slot of the mobile phone for other applications.

It is also preferred in the present invention that at least portions of communication module 100, mobile phone 110, communication system 120 and remote system 130 be capable of communicating in accordance with the Transmission Control Protocol/Internet Protocol (TCP/IP), the suite of communications protocols used to connect hosts on the Internet. TCP/IP itself uses several protocols, the two main ones being TCP and IP. TCP/IP is built into the UNIX and other operating systems and is used by the Internet, making it the de facto standard for transmitting data over networks. Even network operating systems that have their own protocols, such as Netware, also support TCP/IP. Communication module 100 and mobile telephone 110 may also be capable of accessing the Internet using any one or more of the dial-up Integrated Services Digital Network (ISDN) direct line, dial-up Euro-ISDN direct line, dial-up ADSL direct line, and conventional dial-up (i.e., modem via phone lines) standards, as well as by through network connections.

The mobile telephone of the present invention is not limited to embodiments capable of receiving or transmitting voice or data information only, but includes within its scope mobile telephones having web-browsing, e-mail, data storage, fax, 7 and data uploading and/or downloading capabilities. The mobile telephone of the present invention also includes within its scope "smart" mobile telephones that work as both mobile phones and handheld computers, mobile telephones having removable SIM or other cards,.

The Wireless Application Protocol (WAP) finds useful application in some embodiments of communication module 100, mobile telephone 110, communication system 120, and remote system 130 of the present invention owing to its secure specification that permits patient 5 or remote health care provider 136 (such as physician 135) to access information instantly via communication module 100 and mobile telephone 110. WAP supports most wireless networks, including CDPD, CDMA, GSM, PDC, PHS, TDMA, FLEX, ReFLEX, iDEN, TETRA, DECT, DataTAC, and Mobitex. WAP is supported by virtually all operating systems, including PalmOS, EPOC, Windows CE, FLEXOS, OS/9, and JavaOS and perhaps SYMBIAN. WAP employed in conjunction with 3G data transmission is viewed as being a particularly efficacious component in some embodiments of the present invention.

WAP is also particularly suitable for use in connection some embodiments of the present invention because it can accommodate the low memory constraints of handheld devices and the low-bandwidth constraints of a wireless-handheld network. Although WAP supports HTML and XML, the WML language (an XML application) is specifically devised for small screens and one-hand navigation without a keyboard. WML is scalable from two-line text displays up through graphic screens found on items such as smart phones and communicators. WAP also supports WMLScript. It is similar to JavaScript, but makes minimal demands on memory and CPU power because it does not contain many of the unnecessary functions found in other scripting languages.

According to one embodiment of the present invention, an operator or a computer located at remote system 130 initiates remote contact with communication module 100. As discussed above, communication module 100 is capable of down-linking to and uplinking from IMD 10 via telemetry module 101 and antenna or coil 56 and RF transceiver circuit 78 to enable the exchange of data and information between IMD 10 and module 100. For example, an operator or a clinician located at remote computer 130 may initiate down-linking to communication module 100 to perform a routine or a scheduled evaluation of the performance of IMD 10 or communication module 100. Such downlinking may also be initiated by remote computer 130 according to a pre-programmed or predetermined schedule, or in accordance with a prescription previously issued by a physician.

Alternatively, uplinking of information or data contained in IMD 10 may be initiated automatically by IMD 10 or manually by patient 5 to remote computer 130 in response to a detected physiologic event (e.g., cardiac arrhythmia, cardiac tachycardia, syncope, cardiac fibrillation, vital signs of patient 5 being outside normal ranges, etc.) or an IMD performance-related event (e.g., low battery, lead failure, excessive input impedance, etc.) via communication module 100 and mobile telephone 110.

Examples of data or information that may be uplinked to communication module 100 from IMD 10 include, but are in no way limited to, blood pressure data, electrogram data, electrocardiogram data, pH data, oxygen saturation data, oxygen concentration data, QT interval data, activity level data, accelerometer or piezoelectric sensor data, minute ventilation data, transthoracic impedance data, heart rate data, heart rate variability data, ST elevation data, T-wave alternans data, ICD or PCD charging current status, current battery state of charge, drug pump reservoir level status, drug pump reservoir filling status, catheter occlusion data, IMD prescription table, software application versions installed in the IMD, data stored in or acquired by MEDTRONIC CHRONICLE devices, and so on.

Such data may be uplinked in real-time from IMD 10 to communication module 100. Alternatively, such data may be stored in a memory or storage device disposed within IMD 10 for uplink according to a predetermined schedule stored in IMD 10, upon sensing of a threshold physiologic or IMD performance event, or when interrogated by communication module 100.

Communication module 100 may also acquire such data or information from IMD 10 according to a predetermined schedule stored in a memory of communication module 100, and subsequently store such data in memory/storage module 105 until communication module 100 is interrogated by remote computer system 130 and an instruction is received to uplink the information or data to remote system 130. Alternatively, communication module 100 may acquire the information when prompted to do so by patient 5 or by remote computer system 130.

In another embodiment of the present invention, a Personal Data Assistant (PDA) or similar device is employed in place of, in addition to or as part of mobile telephone 110. Combined mobile telephone and PDA devices are specifically contemplated for use in conjunction with the devices, systems and methods of the present invention. Examples of such combined mobile telephones and PDAs include, but are not limited to, the NOKIA Model 9210 device, the MATSUSHITA DILIP MISTRY device, and the COMPAQ iPAQ device. Communication module 100 is linked wirelessly or via a physical connection to the PDA, which in turn is capable of communicating through communication system 120 with remote system 130 and/or remote health care provider 136. The PDA may communicate with and through communication system 120 via wireless means such as mobile telephonic means, RF means, ultrasonic means, infrared means or optical means, or may communicate with and through communication system 120 via traditional telephone wire means.

For example, the PDA or mobile telephone of the present invention can be configured to receive and transmit data by infra-red means to communication system 120 and/or to communication module 110 located on or near patient 5. As patient 5 roams about his home or ventures to other locations such as suitably equipped hotels, hospitals, communities, automobiles or aircraft the PDA remains capable of receiving or transmitting information to or from, for example, infrared sensors or other data communication ports (e.g., BLUETOOTH ports) connected to or forming part of communication system 120, and located in the walls, fixtures or other portions of the environment through which patient 5 is moving or located. Of course, the PDA also remains capable of communicating with communication module 100 (which in turn can communicate with IMD 10) so that data may ultimately be exchanged between remote system 130 and IMD 10.

PDA 110 may also be configured to automatically communicate with IMD 10 or communication system 120, or can be configured to do so upon the prompting or initiation of patient 5, remote health care provider 136, IMD 10 or remote system 130. In such a manner, it is contemplated in the present invention that IMD 10, communication module 100 and/or mobile telephone or PDA 110 can remain in continuous, relatively continuous or at least intermittent communication with remote system 130 and/or health care provider 136 even as patient 5 drives an automobile, goes to work, travels through airports or on aircraft, walks through buildings and so on.

PDA 110 can also Mobile phone 110 may also be configured to accept PCM/CIA cards specially configured to fulfill the role of communication module 100 of the present invention. Alternatively, PDA 110 and/or communication module 100 may receive medical service payment, application programming, controlling and/or other information or data by wireless means (e.g., BLUETOOTH technology, infrared signals, optical signals, etc.) from a chip-based card, module or sensor located in relatively close proximity to communication module 100 and/or PDA 110 and in the possession of patient 5 and/or health care provider 136 or located in sufficiently close proximity to patient 5 or remote health are provider 136 so as to permit reliable communication. PDA 110 may also be an off-the-shelf or specially configured PDA having a plurality sensing electrodes disposed on its backside for sensing ECGs or other signals.

It is further contemplated in the present invention that communication module 100/110 comprise a hand-held mobile telephone having WAP or BLUETOOTH capabilities, or a hand-held mobile telephone having keyboard and/or Liquid Crystal Display (LCD) means for entering or responding to screen displays or information. See, for example, the R380 handset manufactured by Ericcson of Sweden. Monochrome and color LCD and other types of displays are also contemplated for use with the mobile telephone or PDA of the present invention. It is further contemplated in the present invention that an off-the-shelf mobile telephone, or combined PDA and mobile telephone having a removable faceplate, where the original faceplate is removed from the phone or PDA and replaced with a custom faceplate where Keyboardless mobile telephones 110, PDAs 110, or combined mobile telephones/PDAs 110 are also contemplated in the present invention, where patient 5 taps on the display to bring up or enter information in a manner similar to that now employed in, for example, PALM-, HANDSPRING VISOR- or SONY CLIE-brand PDAs.

It is also contemplated that patient 5 interact with communication module 100/110, remote system 130 and/or remote health care provider 136 by tapping on screen icons displayed on a screen incorporated into communication module 100/110. The icons could be, for example, an ambulance icon indicating the need for emergency care, a printer icon indicating that the patient desires to have module 100/110 print out or display a report on the patient's health, a physician icon indicating that the patient wishes to communicate with his remote health care provider, and so on. Incorporated by reference herein, in its entirety, is the "Handbook for the Palm V Organizer", P/N: 405–1139, A/N: 423–1138 published by Palm Computing, Inc. of Santa Clara, Calif. After reading the present disclosure and reviewing the drawings thereof it will become clear that many applications of PDAs can be envisaged or implemented in conjunction with or as part of the various embodiments of the communication systems and methods of the present invention.

In still other embodiments of the present invention, communication module 100 may be incorporated into or onto, or form a part of, a device such as a patch or module adhered or otherwise secured to or located near the skin or clothing of patient 5, or subcutaneously beneath the skin of patient 5, the device being located on, near or in the patient in such a position as to reliable permit telemetric or other communication with IMD 10, as well as with mobile telephone or PDA 110. Mobile telephone or PDA 110 may further be incorporated into such a device, volume, form factor and weight permitting. See, for example, U.S. Pat. No. 5,634, 468 to Platt et al. which describes devices that may be readily adapted in conformance with the immediately foregoing embodiments of the present invention. Such a device or patch may also be configured to hold and deliver beneficial agents to patient 5 in response to receiving an appropriate signal or input from remote health care provider 136, remote system 130, communication module 100 and/or mobile telephone or PDA 110, or IMD 10. That is, such a device may be, by way of example only, an implantable drug pump or dispenser, a non-implantable drug pump or dispenser, a subcutaneous drug pump or dispenser, a patch capable of transmitting or delivering a beneficial agent to patient 5 electrically, mechanically, transdermally, iontophoretically, electrophoretically or otherwise. See, for example, the devices and methods disclosed in U.S. Pat. Nos. 6,126,642; 6,126,637; 6,105,442; 6,095,491; 6,090, 071; 6,086,561; 6,086,560; 6,045,533; 6,063,059; 6,030, 363; 6,027,472; 6,010,482; 6,007,518; 5,993,425; 5,993, 421; 5,980,489; 5,962,794; 5,961,492; 5,957,891; 5,925, 017; 5,921,962; 5,906,703; 5,906,592; 5,885,250; 5,876, 377; 5,858,005; 5,873,857; 5,840,071; 5,830,187; 5,807, 335; 5,807,323; 5,779,676; 5,776,103; 5,743,879; 5,741, 242; 5,735,818; 5,720,729; 5,716,343; 5,700,244; 5,693, 019; 5,693,018; 5,656,032; 5,649,910; 5,569,236; 5,545, 139; 5,531,683; 5,514,090; 5,484,415; 5,484,410; 5,468, 226; 5,433,709; 5,419,771; 5,411,480; 5,385,546; 5,385, 545; 5,374,256; 5,372,578; 5,354,278; 5,336,188; 5,336, 180; 5,334,197; 5,330,426; 5,328,464; 5,314,405; 5,279, 558; 5,267,957; 5,263,940; 5,236,418; 5,205,820; 5,122, 116; and 5,019,047, all assigned to Science Inc. of Bloomington, Minn., at least some of which devices and methods may be modified advantageously in accordance with the teachings of the present invention and the patch, module or other such device described hereinabove.

Referring now to FIG. 8, communication module 100 is illustrated as being capable of communicating with one or a plurality of IMDs 10, 10' or 10". As discussed above, those IMDs are most preferably capable of communicating wirelessly or by other means (such as through interconnecting leads or electrical conductors) with one another. See, for example, U.S. Pat. No. 4,886,064 to Strandberg which describes devices that may be readily adapted in conformance with the immediately foregoing embodiments of the present invention. FIG. 8 also shows that in some embodiments of the present invention remote system 130 may comprise a remote expert or other type of system and/or data center 131, and may further comprise data resource system 112.

Figure 9A:
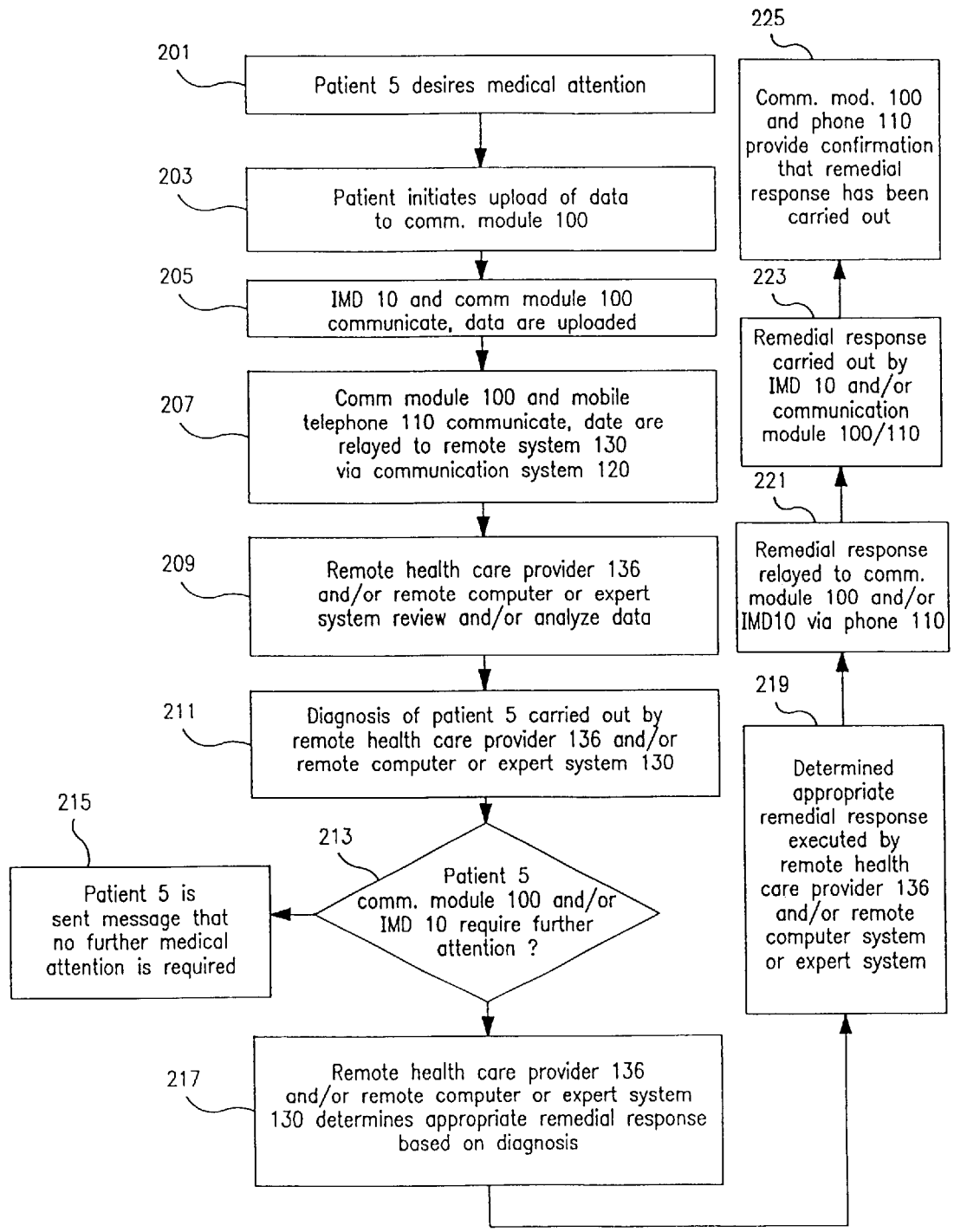
FIGS. 9A and 9B show flow charts for two methods of the present invention relating to patient-initiated communication between IMD 10 and/or communication module 100/mobile telephone or PDA 110 and various components of remote system 130 via communication system 120.
Figure 9B:
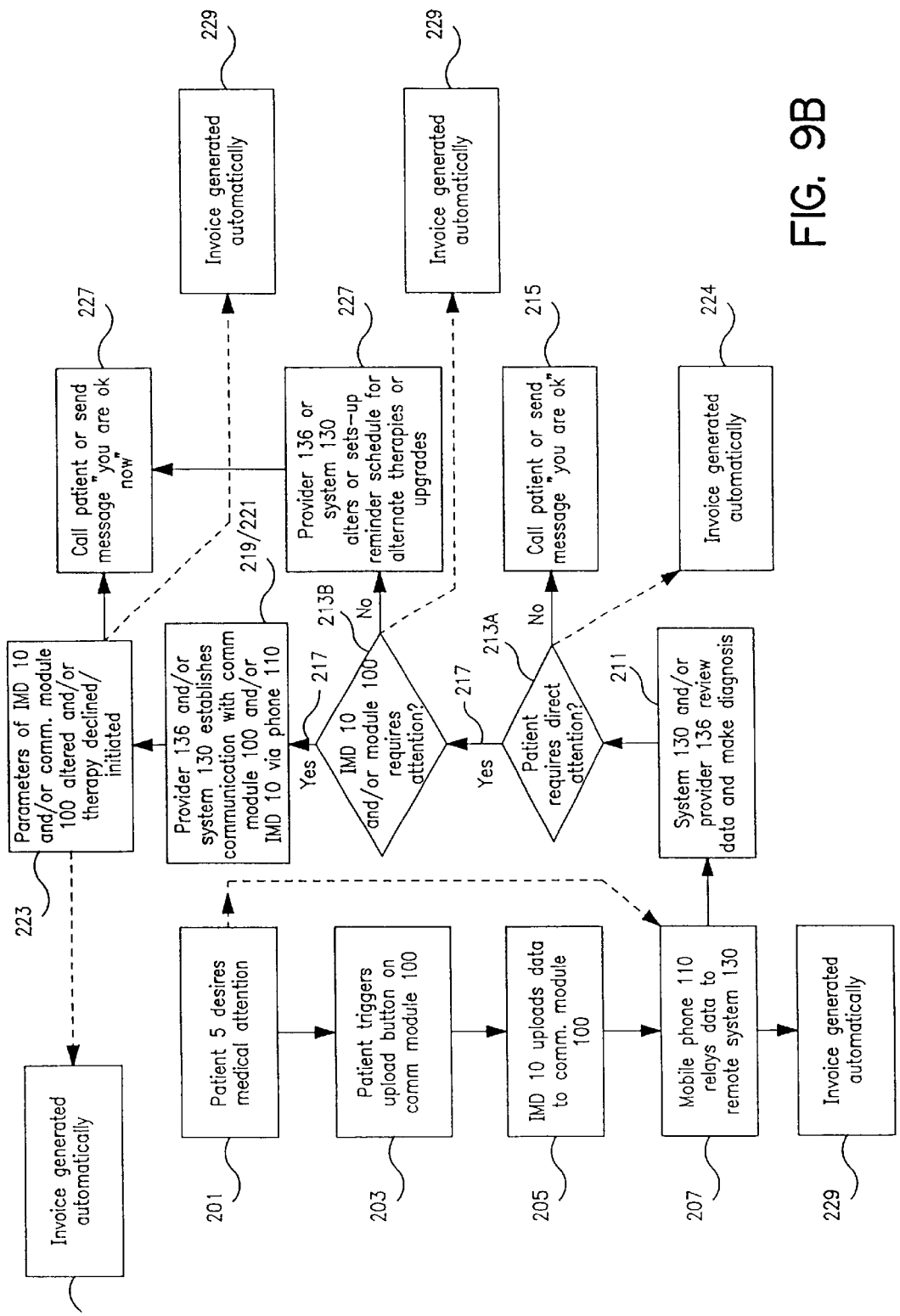

We refer now to FIGS. 9A and 9B, where flow charts for two methods of the present invention relating to patient-initiated communication between IMD 10 and/or communication module 100/mobile telephone or PDA 110 and various components of remote system 130 via communication system 120 are illustrated. It is contemplated in FIGS. 9A and 9B that a PDA, PDA-capable mobile telephone or PDA-type device be optionally employed, either as a replacement for mobile telephone 110, in addition to mobile telephone 110 or as part of mobile telephone 110.

In FIG. 9A, patient 5 at step 201 determines or desires that medical attention should be provided or is required. Such a determination or desire may be based on physiological events which patient 5 or others in his company sense, or may be based merely upon the patient's feeling or desire that his health status or the performance status of his IMD 10 ought to be checked. At step 203, patient 5 initiates upload of data from IMD 10 to communication module 100 by pressing an appropriate button or portion of communication module 100, or issuing an appropriate voice command to same. IMD 10 and communication module 100 then communicate with one another and the data are uploaded. Alternatively, step 203 may be skipped if the desired data have already been uploaded by communication module 100 and are now stored in memory/storage medium 105.

Next, at step 207 the data are transferred from communication module to mobile telephone or PDA 110, and thence on to remote system 130 via communication system 120. At step 209, remote health care provider 136, remote computer system 131 and/or 131', and/or a remote expert computer system evaluate, review and analyze the data. In step 211, diagnosis of the patient's condition (and/or that of IMD 10, communication module 100, and/or mobile telephone or PDA 110) is made by one or more of remote health care provider 136, remote computer system 131 and/or 131', and/or a remote expert computer system.

At step 213, any one or more of remote health care provider 136, remote computer system 131 and/or 131', and/or a remote expert computer system determines, on the basis of the analysis, whether patient 5, communication module 100, mobile telephone or PDA 110 and/or IMD 10 require further attention, correction or intervention. If the analysis reveals that patient 5, communication module 100, mobile telephone or PDA 110 and/or IMD 10 is functioning normally within acceptable limits, patient 5 may be so notified via communication system 120, mobile phone 110 and a visual display or audio signal emitted by communication module 100 (or mobile phone or PDA 110). If, on the other hand, the analysis reveals that a problem exists in respect of any one or more of IMD 10, communication module 100, mobile telephone or PDA 110, and/or patient 5, then remote system 130 and/or health care provider 136 determines an appropriate remedial response to the problem, such as changing the operating parameters of IMD 10, communication module 100 and/or mobile telephone or PDA 110, delivering a therapy to the patient (e.g., a pacing, cardioverting or defibrillating therapy, or administration of a drug or other beneficial agent to patient 5), or instructing patient 5 by audio, visual or other means to do something such as lie down, go to the hospital, call an ambulance, take a medication, or push a button.

The remedial response or therapy determined in step 217 is next executed at step 219 by remote health care provider 136 or remote system 130 and relayed at step 221 via communication system 120 to communication module 100 and/or IMD 10 via mobile phone or PDA 110. After the remedial response or therapy has been delivered, at step 225 communication module and/or mobile telephone 110 may send a confirmatory message to remote system 130 and/or remote care giver 136 indicating that the remedial response or therapy has been delivered to patient 5 and/or IMD 10.

Communication module 100 and/or mobile telephone or PDA 110 may also store data concerning the patient-initiated chain of events described above so that the data may be later retrieved, analyzed, and/or a future therapy determined at least partially on the basis of such data. Such data may also be stored by remote data system 130 for later retrieval, analysis and/or future therapy determination.

It is to be noted that all steps illustrated in FIG. 9A need not be carried out to fall within the scope of the present invention. Indeed, it is contemplated in the present invention that some steps illustrated in FIG. 9A may be eliminated or not carried out, that steps illustrated in FIG. 9A may be carried out in an order different from that shown in FIG. 9A, that steps other than those explicitly illustrated in the Figures may be inserted, and that steps illustrated in different Figures set forth herein (i.e., FIGS. 9B, 9C, 10A, 10B, 11A, 11B, 12a, 12B, 12C, 13A and 13B) maybe combined in various combinations and permutations, and nevertheless fall within the scope of certain embodiments of the present invention. The same considerations hold true for all flow charts and methods illustrated in the drawings hereof and described herein.

In FIG. 9B, some of the same steps shown in FIG. 9A are executed. Invoice generation steps 229 may be automatically generated in conjunction with or in response to one or more of steps 201, 207, 213A, 213B, 217, 225 or 227 being carried out. The invoices so generated may be electronically transmitted to appropriate locations for further processing and billing. The amounts of the invoices so generated may depend, for example, on the number, type and/or frequency of services provided to patient, the type or identification indicia stored in communication module 100 or IMD 10, and other factors.

Figures 2, 9C:
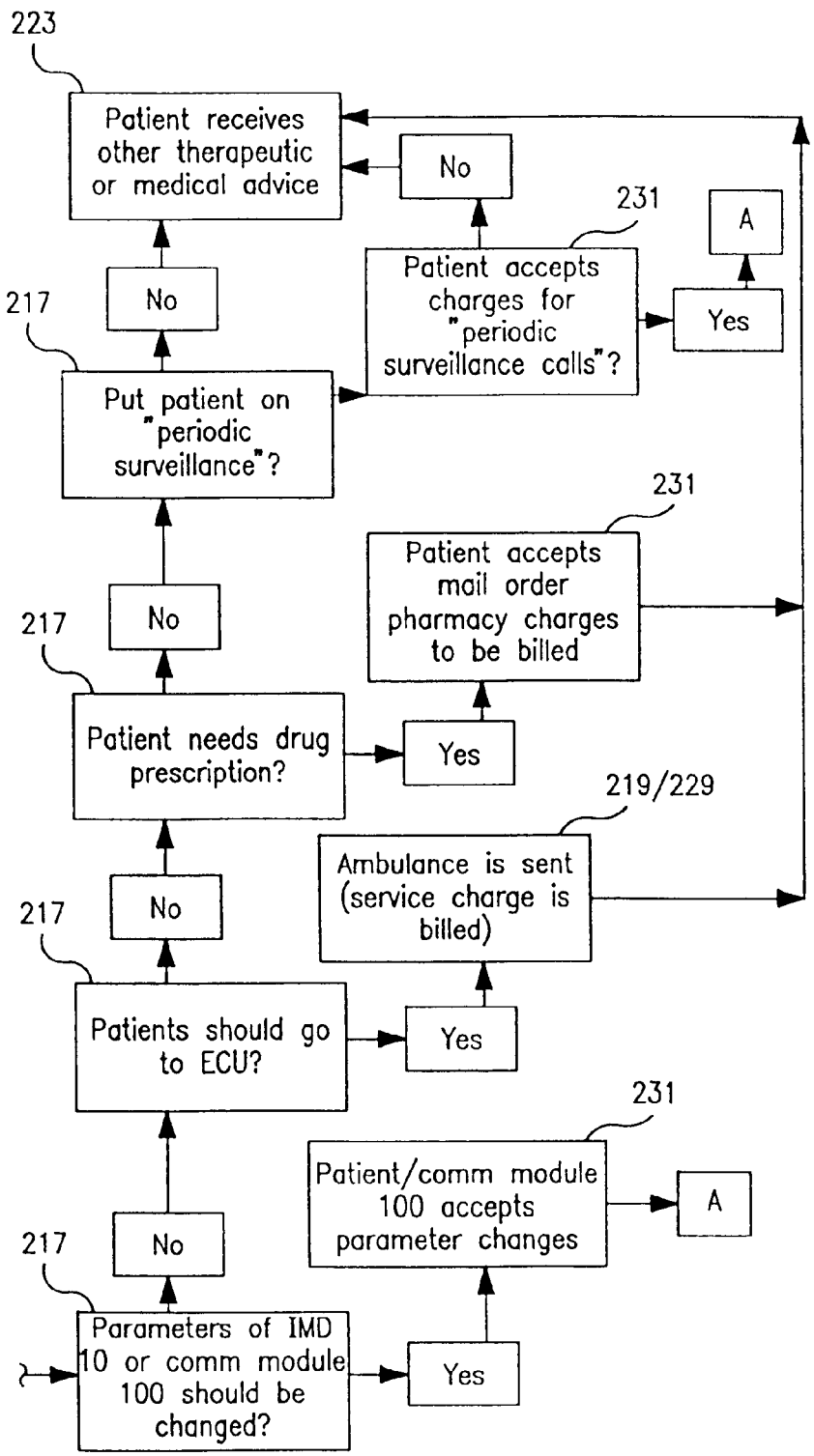
FIG. 9C shows another method of the present invention related to the methods illustrated in FIGS. 9A and 9B.

FIG. 9C shows another method of the present invention related to the methods illustrated in FIGS. 9A and 9B. In FIG. 9C patient 5 determines that medical attention is required or desirable. Steps 203 and 205 are equivalent to those described above in respect of FIGS. 9A and 9B. At step 206a, uploaded data from IMD 10 or data previously uploaded from IMD 10 stored in communication module 100 and/or mobile telephone or PDA 110 are compared to pre-programmed or stored data and/or data ranges to help establish whether the uploaded data fall within a safe range.

If the comparison of data reveals that the uploaded data fall into a safe range, then patient 5 is so alerted at step 227. If the comparison of data reveals that the uploaded data do not fall within the safe range represented by the pre-programmed or stored data, then steps 213, 217 and 219 illustrated in FIGS. 9A and/or 9B are carried out. Patient 5 or patient 5's health care provider or insurer may be billed for the request for medical attention made at step 201 or any or all of steps 229.

When a diagnostic assessment, remedial response or therapy is executed and relayed to IMD 10, communication module 100 and/or mobile telephone or PDA 110, charges may be billed to patient 5 or patient 5's health care provider or insurer at a fixed rate or at a rate proportional to the amount of time required to relay or execute the assessment, response or therapy, or at a rate which depends upon the particular type of information, assessment, remedial response or therapy being delivered to patient 5.

Other steps shown in FIG. 9C may also be carried out, such as having prescription drugs mailed to patient 5 and billed to an insurance company or reimbursement authority at steps 217/231 in response to receiving appropriate and timely authorization from patient 5, remote health care provider 136 and/or an insurer, placing patient 5 on periodic surveillance for a fee and/or requesting that patient 5 authorize charges for such surveillance at steps 217/231, determining patient 5 should be taken to the emergency unit of a hospital, ordering an ambulance for patient 5 and billing charges for the ambulance service to the appropriate entity at steps 217/229, and determining at step 217 that the operating parameters of IMD 10, communication module 100 and/or mobile phone or PDA 110 need to or should be updated or changed, followed by requesting at step 231 that patient 5, health care provider 136 or an insurer confirm acceptance of charges for such parameter updates or changes before or at the same time as they are implemented.

In other methods of the present invention, it is contemplated that pre-paid telephone or other magnetic cards be used in conjunction with communication module 100 and/or mobile telephone or PDA 110 as a means of authorizing the provision of services, medications, prescriptions and information. Such pre-paid cards could be employed in conjunction with telephone service providers and their billing and invoicing systems. Referring briefly to FIGS. 6A through 6C, and by way of example only, when telephone/PDA 110 establishes communication via communication system 120, the telephone service provider involved in carrying out at least some of the functions of communication system 120 can keep track of and calculate charges made using pre-paid cards by a particular patient 5. The amount of charges billed against a pre-paid card could be made dependent on the complexity of the procedures and services which are initiated by patient 5, IMD 10 and/or communication module 100/mobile telephone or PDA 110. For example, a routine check of the battery state of charge of IMD 10 could cost a low number of magnetic impulses stored on the pre-paid card, while an instruction to deliver a tachycardia intervention originating from remote system 130 could cost a high number of magnetic impulses stored on the pre-paid card.

Additionally, the communication system of the present invention can be configured to store and tally bonus points for patient 5, where the number of bonus points stored for patient 5 depends, for example, on the number of transactions patient 5 has engaged in or initiated using the methods, systems or devices of the present invention. For example, if a pharmaceutical company conducting a clinical trial or study involving IMD 10 and/or a prescription drug manufactured by the company that is being used in the study wishes to purchase data from patient 5 or patient 5's IMD 10, communication module 100 and/or mobile telephone or PDA 110, and patient 5 authorizes such purchase, patient 5's pre-paid card could be credited with a number of extra magnetic pulses or extra bonus points could be stored in his behalf, by, for example, a telephone service provider. At some point patient 5 can receive a cash or other reimbursement according to the total number of bonus points he has accumulated.

It is important to note that the billing inquiry, acceptance, authorization and confirmation steps illustrated in the various Figures hereof or described herein may include communications with and determinations made by an insurer having access to at least portions of the various communication networks described herein. Additionally, it is important to point out that it is contemplated in the present invention that a telephone service provider can be involved in the automated invoicing and billing methods of the present invention, and that patient 5 and/or remote system 130 and/or remote health care provider 136 be involved or be permitted to be involved in the service request initiation, remedial action determination and execution, and billing inquiry, acceptance, authorization and confirmation steps illustrated in the various Figures hereof and described herein.

Thus, it will now become apparent that one important aspect of the various embodiments of the present invention is automated and streamlined billing and invoicing methods that increase patient empowerment, lower health care costs and result in the delivery of more customized and timely therapies and remedial actions to patient 5. For example, if in any of FIGS. 9A through 9C patient 5 caries out step 201 by, e.g., pressing an appropriate button, a screen or display on communication module 100 and/or mobile phone or PDA 110, one or more messages could be displayed to patient 5 such as: ""Your heart rate is OK", "You are not in atrial fibrillation", "Call the hospital Immediately", or "Go to Hospital".

Inquiries made by patient 5, communication module 100, IMD 10, mobile phone or PDA 110, remote health care provider 136 or remote system 130, and the invoices generated in response to those inquiries being made, may be separated into three main categories:

(i) patient visible inquiries, where the patient confirms the inquiry he wishes to make, an invoice is generated automatically, and the invoice is logged;

(ii) patient relayed inquiries, where the patient is requested to carry out an action such as taking a medication or confirming that he wishes to receive a therapy before an invoice is generated automatically and the invoice is logged;

(iii) patient invisible inquiries, where IMD 10, communication module 100, mobile phone or PDA 110, remote system 130 or remote health care provider 136 initiates communication for patient monitoring, clinical study monitoring, therapeutic, clinical outcome study or other purposes to thereby minimize unnecessary patient-physician or patient-hospital interaction.

Phone or PDA 110 and/or communication module 100 could be provided at no up-front cost to patient 5. Once patient 5 activates or requests a service using phone or PDA 110 and/or communication module 100, the bills for services incurred subsequently or simultaneously could be charged through a telephone company operating in a business alliance with remote health care provider 136.

Such automated billing methods and health care delivery services have the potential to reduce overall health care costs and improve the timely and efficient delivery of therapies and remedial responses to patient 5 because remote health care provider 136 would be monitoring the health status of patient 5 and/or delivering therapies to patient 5 without the involvement of expensive institutions such as hospitals or clinics. Accordingly, the methods and procedures of some embodiments of the present invention could deduces the number of unnecessary emergency room visits or physician consultations made by patient 5.

Automated invoicing may also be carried out at the opposite end of the system of the present invention, such as at remote health are provider 136 or physician 135, such that when remote health care provider 136 and/or physician 135 requests delivery of information or a therapy to patient 5, an invoice is automatically generated and is billed, for example, through a telephone company or to an insurance company or reimbursement authority.

Review and authorization of government reimbursements for services charges incurred as a result of using the various systems and methods of the present invention could also be automated. Reimbursement costs, patient identities and other data associated with reimbursement could be tracked and centralized very efficiently and easily using the methods of the present invention. IMD 10, mobile phone or PDA 110 an/or communication module 100 could have a patient identity code stored therein for transmittal to remote system 130. Such a code could be employed at remote system 130 or elsewhere to verify the identity of patient 5 or the type or model of IMD 10, communication module 100 and/or mobile phone or PDA 110, and receipt of such a code could be employed as a precondition to receiving information, remedial action or a therapy from remote system 130.

In other billing methods of the present invention, a server located at remote health care provider 136 contacts patient 5 via mobile phone or PDA 110 and inquires whether patient 5 would like to receive a therapy, remedial action or information from remote system 30 and/or health care provider 136 or another source, the provision of which will result in patient 5 or an insurance company being billed. Patient 5 must confirm he wishes to receive such information, remedial action or therapy before delivery of same. Insurance company or reimbursement authority authorization could be included in such a method as a prerequisite to receiving the information, remedial action or therapy.

In one method of the present invention, remote system or server 130 automatically contacts patient 5 according to a predetermined schedule, upon receiving instructions to do so from another source (e.g., a physician, or a data mining project which results in detecting a trend or symptom characterizing patient 5 and other like individuals), or in response to receiving information relayed to remote system 130 as a result of IMD 10 and/or communication module 100/mobile phone or 110 initiating communication with remote system 130 in response to detecting a condition in patient 5 or his environs that requires monitoring of patient 5, analysis of data from patient 5 or the execution of remedial action.

In another method of the present invention, patient 5 or her insurance company leases or rents module 100 and/or mobile phone or PDA 110 on a daily, weekly, monthly, quarterly, annual or other basis. In such a method, module 100 and/or mobile phone or PDA 110 are leased or rented for the period of time required to monitor IMD 10 implanted in patient 5, deliver remedial action or therapy to patient 5 via IMD 10 and/or another medical device, or acquire data from IMD 10 and/or communication module 100/mobile phone or PDA 110. For example, patient 5 may be a terminally or seriously ill patient who is not expected to survive longer than a period of months or weeks, where economic considerations or reimbursement policies might otherwise dictate that one or more of the various systems or methods of the present invention not be employed to treat or monitor patient 5 because of prohibitively high costs. Once patient 5 becomes well again or dies, module 100 and/or mobile phone or PDA 110 may be used to treat or monitor other patients, thereby lowering patient, insurance, reimbursement, hospital, physician costs while improving the quality and type of care administered to patient 5.

In another method of the present invention, IMD 10 may be provided to and implanted within patient 5 and be capable of effecting rather broad features and functionalities that may be selectively and remotely activated or de-activated under the control of remote system 130 communicating with IMD 10 via communication system 120 and mobile phone or PDA 110 and/or communication module 100. In such a method, it is contemplated that perhaps only certain of the available features of IMD 10 may be required to treat and/or monitor patient 5, and that only certain or all of those features may be selected initially by a physician. Subsequently, and most preferably after data have been acquired by IMD 10 and transferred therefrom to remote system 130 using the communication system of the present invention or in response to information provided or inquiries made by patient 5, physician 135, remote health care provider 136 and/or remote system 130, certain of the features or functionalities possessed by IMD 10 may be terminated or activated.

For example, it may be determined that IMD 10 has not been optimally programmed for a particular patient 5 once sufficient data have been acquired and evaluated remotely at system 130. New IMD or updated patient specific operating parameters can then be downloaded to IMD 10, and/or IMD functionalities or features can be enabled or disabled in IMD 10. According to such a method, IMD 10 and/or communication module 100/mobile phone or PDA 110 may be provided initially to patient 5 with a minimum number of features or functionalities, and therefore sold at the lowest possible initial cost. After an initial trial operation period during which data are collected from IMD 10 and/or communication module 100/mobile phone or PDA 110, or during which feedback is elicited from patient 5 and/or physician 135, it may be desirable to update or change the functionality of IMD 10 so as to offer more advanced therapy or monitoring capabilities to patient 5 via IMD 10. Once such updates or changes are implemented in IMD 10 a new invoice is generated reflecting the incremental cost of adding the new capabilities or features to IMD 10 and/or communication module 100/mobile phone or PDA 110.

In accordance with such methods of the present invention, patients 5 may in some cases be able to leave the hospital earlier than might otherwise be possible because of the built-in remote monitoring and adaptability capabilities of the system of the present invention. Additionally, the invoices generated in accordance with the various methods of the-present invention could result in smaller payments being made over longer periods of time, thereby further lowering overall health care costs while at the same time improving the quality and type of care provided to patients 5.

It will now become clear that an almost infinite number of combinations and permutations of the various steps of the invoicing methods of the present invention may be conceived of and implemented in accordance with the teachings of the present invention. For example, at or after step 217 in any of FIGS. 9A, 9B and 9C a report may be generated at remote system 130 or at communication module 100 and/or mobile telephone or PDA 110. Or remote system 130 or remote health care provider 136 may, in response to receiving a request for medical attention from patient 5, IMD 10 and/or communication module 100/mobile telephone or PDA 110, contact a physician or specialist indicated in a database of remote system 130 as being patient 5's emergency contact to request that the physician or specialist review data or reports provided by the system of the present invention and subsequently adjust the operating parameters of IMD 10. Or IMD 10 may be re-programmed with new software or algorithms in response to review and analysis of information obtained remotely from IMD 10. Or invoices, reports, confirmations of billing, confirmations of therapy delivery, and so on generated by the various methods of the present invention may be automatically transmitted in a pre-programmed or predetermined manner to insurance companies, reimbursement authorities, hospitals, physicians, patients, health care professionals or other persons or institutions via fax, e-mail, postal service, express mail, voice mail, SMA or other known communication means.

The methods and devices of the present invention could also permit the process of obtaining patient consents to the release of medical information to be streamlined. For example, patient 5 could be interrogated on an as-required basis via mobile phone or PDA 110 to provide confirmation that the data or information that has been acquired, is being acquired, or will be acquired from or relating to him may be released to certain entities or personnel, such as insurance companies, clinical study managers, physicians, nurses, hospitals and governmental or academic institutions. A log of the patient's responses to such inquiries could be maintained in the memory or storage of communication module 100 or remote system 130.

As mentioned briefly above, the various methods and devices of the present invention may also be configured and adapted to more efficiently and cost-effectively administer clinical monitoring studies and clinical outcome studies. In accordance with one embodiment of the present invention, IMDs implanted in patients 5 and/or corresponding communication modules 100 or mobile phones or PDAs 110, where patients 5 are participating in clinical outcome studies and/or clinical monitoring studies, are interrogated for data required or desired for purposes of completing such studies. Devices 10, 100 and/or 110 are remotely interrogated using remote system 130 and communication system 120. Patients 5 are remotely interrogated for the required data on an as-required basis, or according to a predetermined schedule, either automatically or under the direct or indirect control of remote health care provider 136. According to this method of the present invention, there is no need for patients having to go to clinics or hospitals to have data uploaded from their IMDs so that data required for the studies may be acquired. Accordingly, patient, clinical study and overall health care costs are reduced, while the rate at which such studies may be completed, and the scope, amount and types of clinical data which may be acquired using such methods, are increased.

Figure 10A:
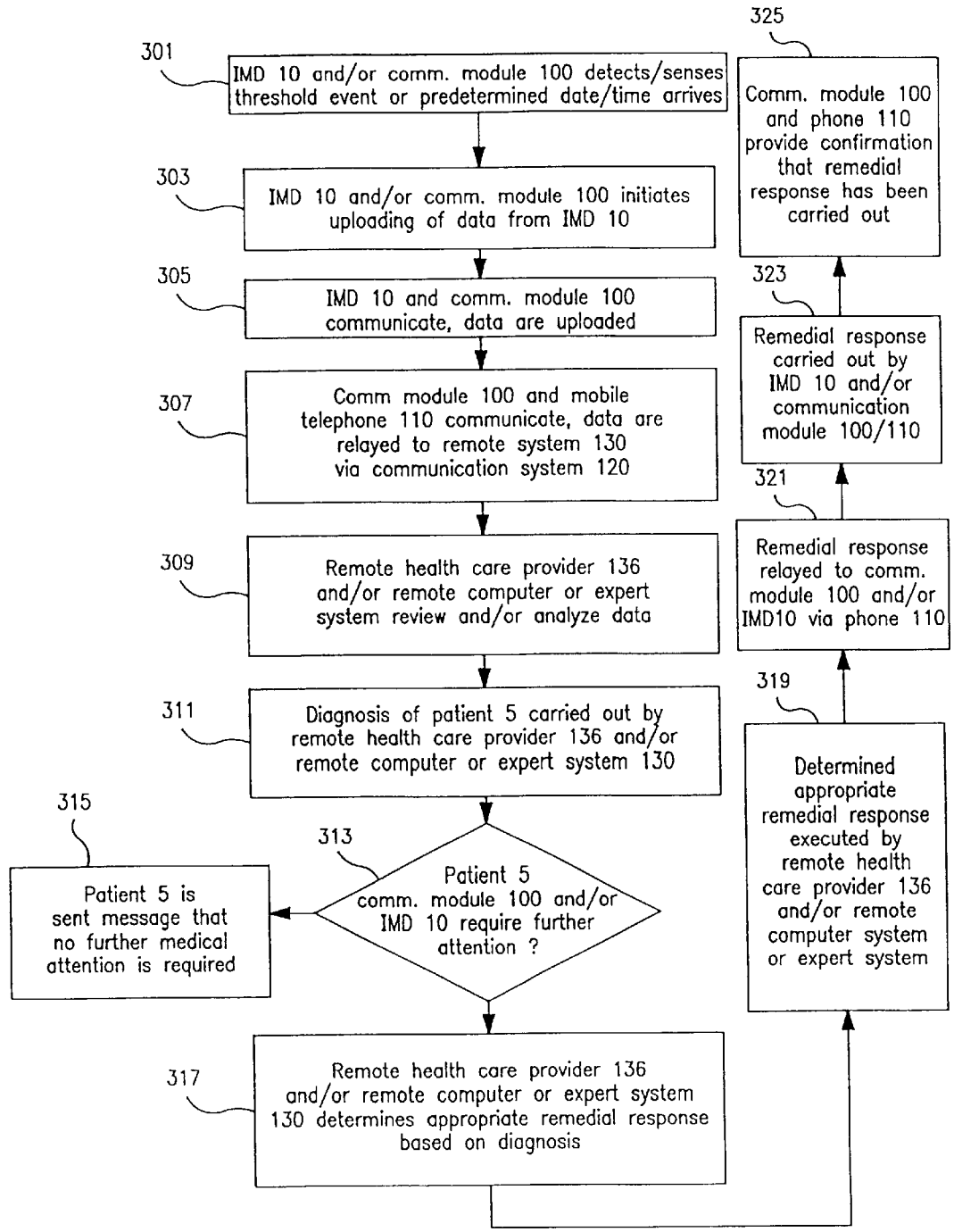
FIGS. 10A and 10B show flow charts for two methods of the present invention relating to device-initiated communication between IMD 10 and/or communication module 100/mobile telephone or PDA 110 and various components of remote system 130 via communication system 120.
Figure 10B:
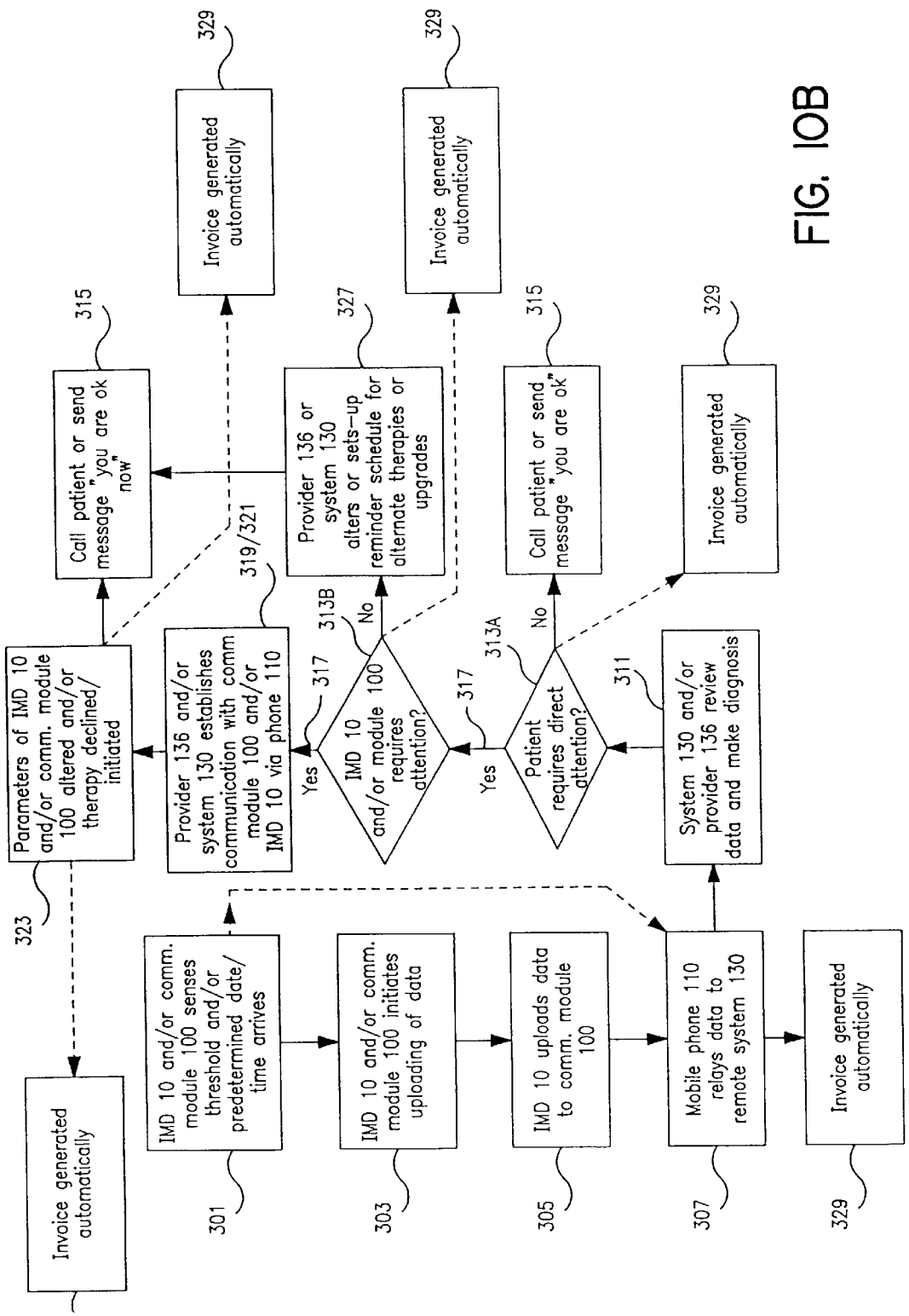

We refer now to FIGS. 10A and 10B, where flow charts for two methods of the present invention relating to device-initiated communication between IMD 10 and/or communication module 100/mobile telephone or PDA 110 and various components of remote system 130 via communication system 120 are illustrated. It is contemplated in FIGS. 10A and 10B that a PDA, PDA-capable mobile telephone or PDA-type device be optionally employed, either as a replacement for mobile telephone 110, in addition to mobile telephone 110 or as part of mobile telephone 110.

In FIG. 10A, IMD 10 and/or communication module 100 and/or mobile telephone or PDA 110 at step 301 senses a threshold event, a predetermined time arrives, or makes a determination that medical attention or information should be provided or is required. Such a threshold sensing event, predetermined time or determination may be based, for example, on physiological events sensed in patient 5, a predetermined schedule or calculations made by IMD 10 and/or communication module and/or mobile telephone or PDA 110 using data sensed or provided by IMD 10.

At step 303, IMD 10 and/or communication module 100 and/or mobile telephone or PDA 110 automatically initiates the upload of data from IMD 10 to communication module 100 and/or mobile telephone or PDA 110. IMD 10 and communication module 100 then communicate with one another and the data are uploaded. Alternatively, step 303 may be skipped if the required data have already been uploaded into communication module 100 and/or mobile telephone or PDA 110 and are now stored in memory/storage medium 105.

Next, at step 307, the data are automatically transferred from communication module 100 to mobile telephone or PDA 110, if required, and thence on to remote system 130 via communication system 120. At step 309, remote health care provider 136, remote computer system 131 and/or 131', and/or a remote expert computer system evaluate, review and analyze the data. In step 311, diagnosis of the patient's condition (and/or that of IMD 10, communication module 100, and/or mobile telephone or PDA 110) is made by one or more of remote health care provider 136, remote computer system 131 and/or 131', and/or a remote expert computer system.

At step 313, any one or more of remote health care provider 136, remote computer system 131 and/or 131', and/or a remote expert computer system determines, on the basis of the analysis, whether patient 5, communication module 100, mobile telephone or PDA 110 and/or IMD 10 require further attention, correction or intervention. If the analysis reveals that patient 5, communication module 100, mobile telephone or PDA 110 and/or IMD 10 is functioning normally within acceptable limits, IMD 10 and/or communication module 100 and/or mobile telephone or PDA 110, or patient 5, may be so notified via communication system 120, mobile phone 110, and a visual display or audio signal may be emitted by communication module 100 (or mobile phone or PDA 110).

If, on the other hand, the analysis reveals that a problem exists in respect of any one or more of IMD 10, communication module 100, mobile telephone or PDA 110, and/or patient 5, then remote system 130 and/or health care provider 136 determines an appropriate remedial response to the problem, such as changing the operating parameters of IMD 10, communication module 100 and/or mobile telephone or PDA 110, delivering a therapy to the patient (e.g., a pacing, cardioverting or defibrillating therapy, or administration of a drug or other beneficial agent to patient 5), or instructing patient 5 by audio, visual or other means to do something such as lie down, go to the hospital, call an ambulance, take a medication, or push a button.

The remedial response or therapy determined in step 317 is next executed at step 319 by remote health care provider 136 or remote system 130 and relayed at step 321 via communication system 120 to communication module 100 and/or IMD 10 via mobile phone or PDA 110. After the remedial response or therapy has been delivered, at step 325 communication module and/or mobile telephone or PDA 110 may send a confirmatory message to remote system 130 and/or remote care giver 136 indicating that the remedial response or therapy has been delivered to patient 5 and/or IMD 10.

Communication module 100 and/or mobile telephone or PDA 110 may also store data concerning the patient-initiated chain of events described above so that the data may be later retrieved, analyzed, and/or a future therapy determined at least partially on the basis of such data. Such data may also be stored by remote data system 130 for later retrieval, analysis and/or future therapy determination.

It is to be noted that all steps illustrated in FIG. 10A need not be carried out to fall within the scope of the present invention. Indeed, it is contemplated in the present invention that some steps illustrated in FIG. 10A may be eliminated or not carried out, that steps illustrated in FIG. 10A may be carried out in an order different from that shown in FIG. 10A, that steps other than those explicitly illustrated in the Figures may be inserted, and that steps illustrated in different Figures set forth herein (i.e., FIGS. 9A, 9B, 9C, 10B, 11A, 11B, 12a, 12B, 12C, 13A and 13B) may be combined in various combinations and permutations, and nevertheless fall within the scope of certain embodiments of the present invention. The same considerations hold true for all flow charts and methods illustrated in the drawings hereof and described herein.

In FIG. 10B, some of the same steps shown in FIG. 10A are executed. Invoice generation steps 229 may be automatically generated in conjunction with or in response to one or more of steps 301, 307, 311, 313A, 313B, 317, 325 or 327 being carried out. The invoices so generated may be electronically transmitted to appropriate locations for further processing and billing. The amounts of the invoices so generated may depend, for example, on the number, type and/or frequency of services provided to patient, the type or identification indicia stored in communication module 100 or IMD 10, and other factors.

Figure 11A:
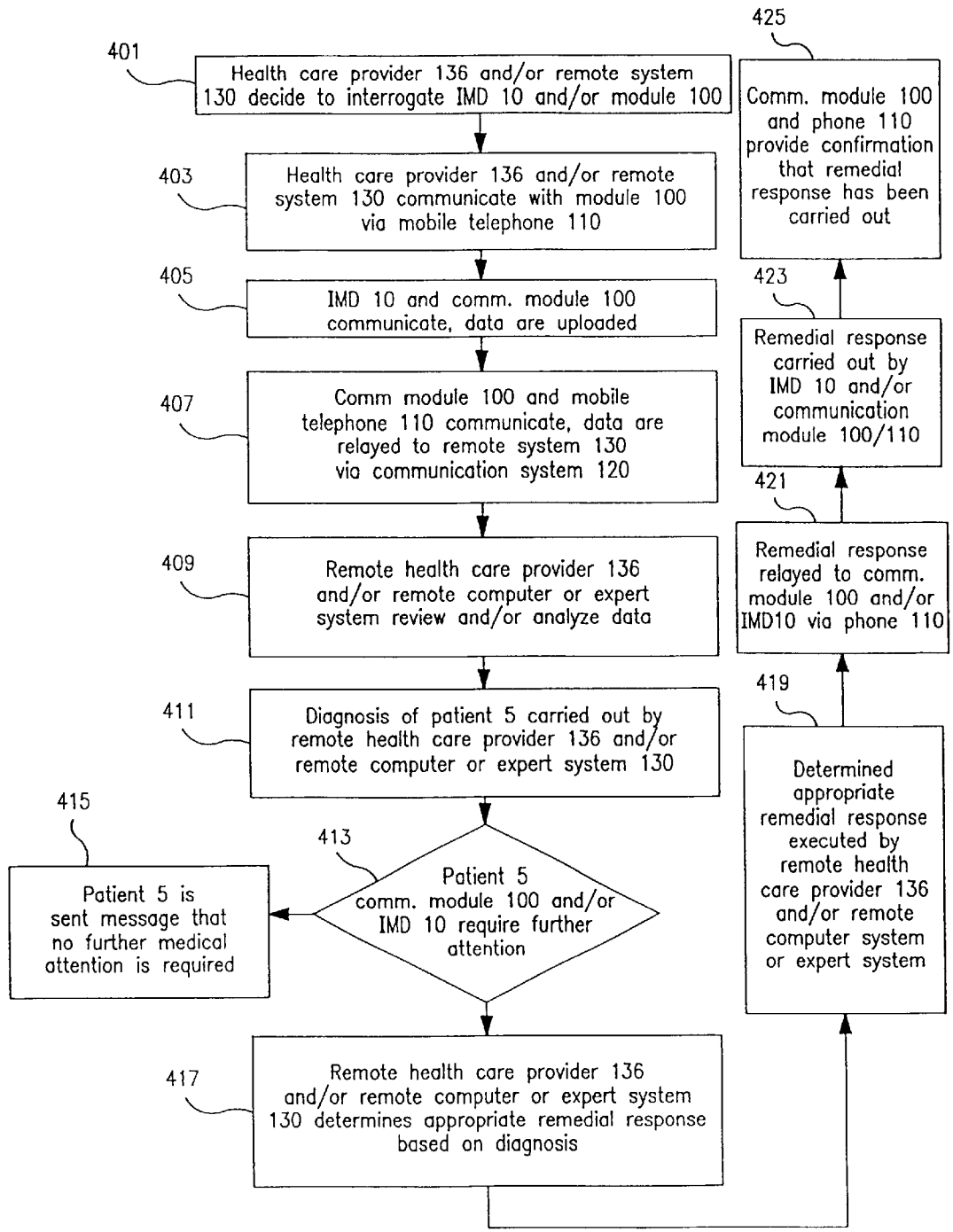
Figure 1B:
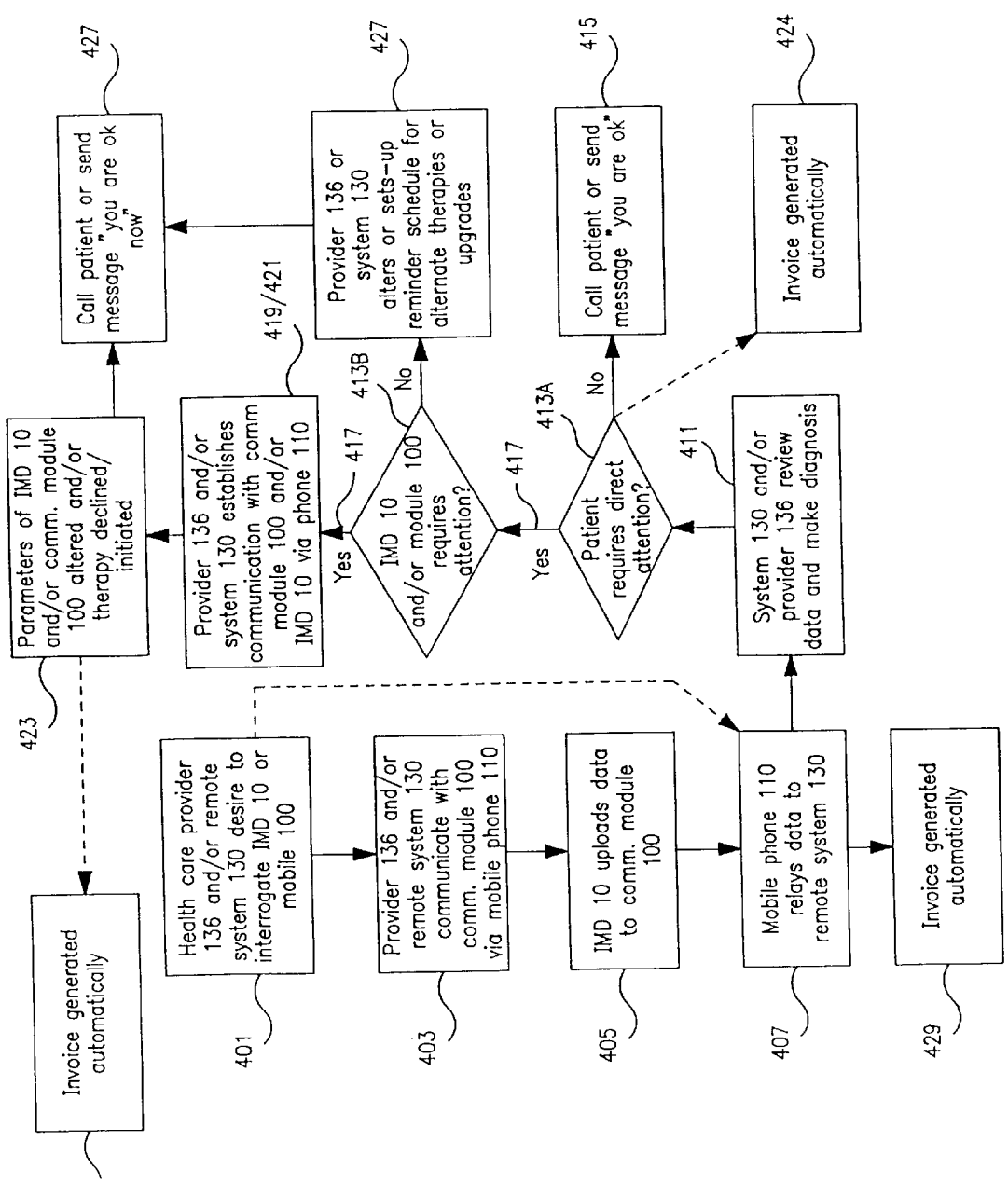

We refer now to FIGS. 11A and 11B, where flow charts for two methods of the present invention relating to remote system 130 and/or remote health care provider 136 (which may include or even be limited to physician 135) initiated communication between IMD 10 and/or communication module 100 and/or mobile telephone or PDA 110 and various components of remote system 130 via mobile telephone or PDA 110 are illustrated. It is contemplated in FIGS. 11A and 11B that a PDA, PDA-capable mobile telephone or PDA-type device be optionally employed, either as a replacement for mobile telephone 110, in addition to mobile telephone 110 or as part of mobile telephone 110.

In FIG. 11A, remote system 130 and/or remote health care provider 136 determines that medical attention or information should be provided to patient 5 or is required by patient 5. A determination that such attention or information should be provided may be based on data or information previously relayed to remote system 130 or remote health care provider 136 by IMD 10 and/or communication module 100 and/or mobile telephone which is subsequently analyzed to determine if a remedial response is required or desirable, information contained in or generated by remote system 130 or an outside source of information (such as patient data monitoring intervals suggested or formulated by the manufacturer of IMD 10), or the action of health care provider 136.

At step 403, remote system 130 and/or remote health care provider 136 initiates upload of data from IMD 10 to communication module 100 and/or mobile telephone or PDA 110 via communication system 120. IMD 10 and communication module 100 then communicate with one another and the data are uploaded. Alternatively, step 403 may be skipped if the desired data have already been uploaded by communication module 100 and/or mobile telephone or PDA 110 and are now stored in memory/storage medium 105. Next, at step 407, the data are transferred from communication module to mobile telephone or PDA 110, and thence on to remote system 130 via communication system 120. At step 409, remote health care provider 136, remote computer system 131 and/or 131', and/or a remote expert computer system evaluate, review and analyze the data.

At step 411, diagnosis of the patient's condition (and/or that of IMD 10, communication module 100, and/or mobile telephone or PDA 110) is made by one or more of remote health care provider 136, remote computer system 131 and/or 131', and/or a remote expert computer system. At step 413, any one or more of remote health care provider 136, remote computer system 131 and/or 131', and/or a remote expert computer system determines, on the basis of the analysis, whether patient 5, communication module 100, mobile telephone or PDA 110 and/or IMD 10 require further attention, correction or intervention.

If the analysis reveals that patient 5, communication module 100, mobile telephone or PDA 110 and/or IMD 10 is functioning normally within acceptable limits, patient 5 may be so notified via communication system 120, mobile phone 110 and a visual display or audio signal emitted by communication module 100 (or mobile phone or PDA 110).

If, on the other hand, the analysis reveals that a problem exists in respect of any one or more of IMD 10, communication module 100, mobile telephone or PDA 110, and/or patient 5, then remote system 130 and/or health care provider 136 determines an appropriate remedial response to the problem, such as changing the operating parameters of IMD 10, communication module 100 and/or mobile telephone or PDA 110, delivering a therapy to the patient (e.g., a pacing, cardioverting or defibrillating therapy, or administration of a drug or other beneficial agent to patient 5), or instructing patient 5 by audio, visual or other means to do something such as lie down, go to the hospital, call an ambulance, take a medication, or push a button.

The remedial response or therapy determined in step 417 is next executed at step 419 by remote health care provider 136 or remote system 130 and relayed at step 421 via communication system 120 to communication module 100 and/or IMD 10 via mobile phone or PDA 110. After the remedial response or therapy has been delivered, at step 425 communication module and/or mobile telephone 110 may send a confirmatory message to remote system 130 and/or remote care giver 136 indicating that the remedial response or therapy has been delivered to patient 5 and/or IMD 10. Communication module 100 and/or mobile telephone or PDA 110 may also store data concerning the patient-initiated chain of events described above so that the data may be later retrieved, analyzed, and/or a future therapy determined at least partially on the basis of such data. Such data may also be stored by remote data system 130 for later retrieval, analysis and/or future therapy determination.

It is to be noted that all steps illustrated in FIG. 11A need not be carried out to fall within the scope of the present invention. Indeed, it is contemplated in the present invention that some steps illustrated in FIG. 11A may be eliminated or not carried out, that steps illustrated in FIG. 11A may be carried out in an order different from that shown in FIG. 11A, that steps other than those explicitly illustrated in the Figures may be inserted, and that steps illustrated in different Figures set forth herein (i.e., FIGS. 9A, 9B, 9C, 10A, 10B, 11B, 12a, 12B, 12C, 13A and 13B) be combined in various combinations and permutations, and nevertheless fall within the scope of certain embodiments of the present invention. The same considerations hold true for all flow charts and methods illustrated in the drawings hereof and described herein.

In FIG. 11B, some of the same steps shown in FIG. 11A are executed. Invoice generation steps 429 may be automatically generated in conjunction with or in response to one or more of steps 401, 407, 413A, 413B, 417, 423 or 427 being carried out. The invoices so generated may be electronically transmitted to appropriate locations for further processing and billing. The amounts of the invoices so generated may depend, for example, on the number, type and/or frequency of services provided to patient, the type or identification indicia stored in communication module 100 or IMD 10, and other factors.

In the methods illustrated in FIGS. 11A and 11B it is further contemplated that IMD 10 be remotely interrogated by remote system or server 130 that automatically communicates with IMD 10 via communication module 100 and/or mobile telephone or PDA 110, and that data from IMD 10 and/or communication module 100 and/or mobile telephone or PDA 110 be retrieved therefrom automatically.

Figure 12A:
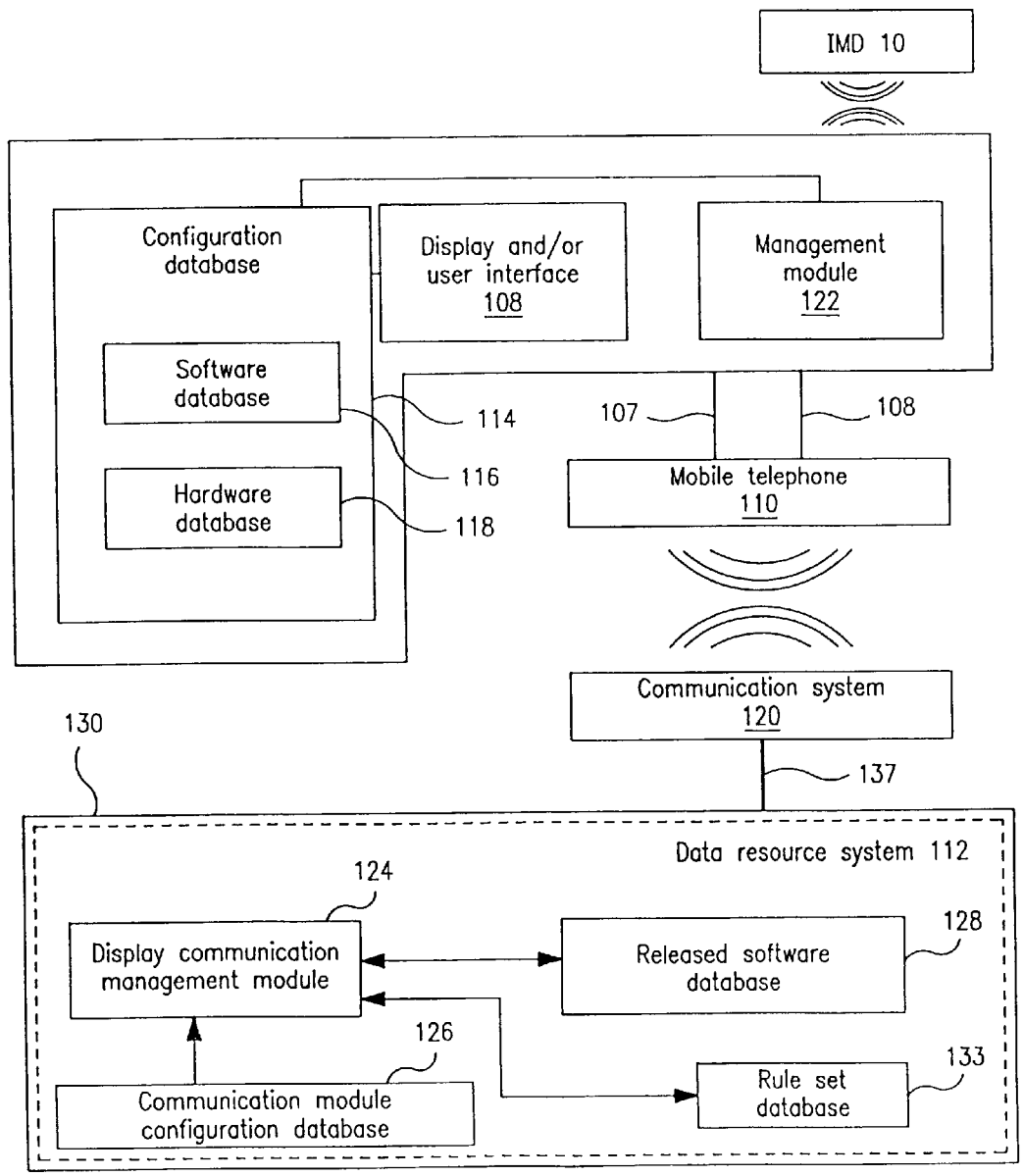
FIG. 12A shows one embodiment of communication module 100, mobile telephone or PDA 110, communication system 120, and remote computer system 130 of the present invention.

FIG. 12A shows one embodiment of communication module 100, mobile telephone or PDA 110, communication system 120, and remote computer system 130 of the present invention, where remote computer system 130 comprises remote expert system 131 and data resource system 112. Here, communication module 100 includes configuration database 114, which further comprises software database 116 and hardware database 118. Patient interface module 115 and management module 122 may also be contained in communication module 100. Those systems preferably form high level software systems that may be remotely or otherwise upgraded as the need arises through the action and downlinking of software from remote computer system 130, or alternatively through on-site software upgrading.

Figure 12B:
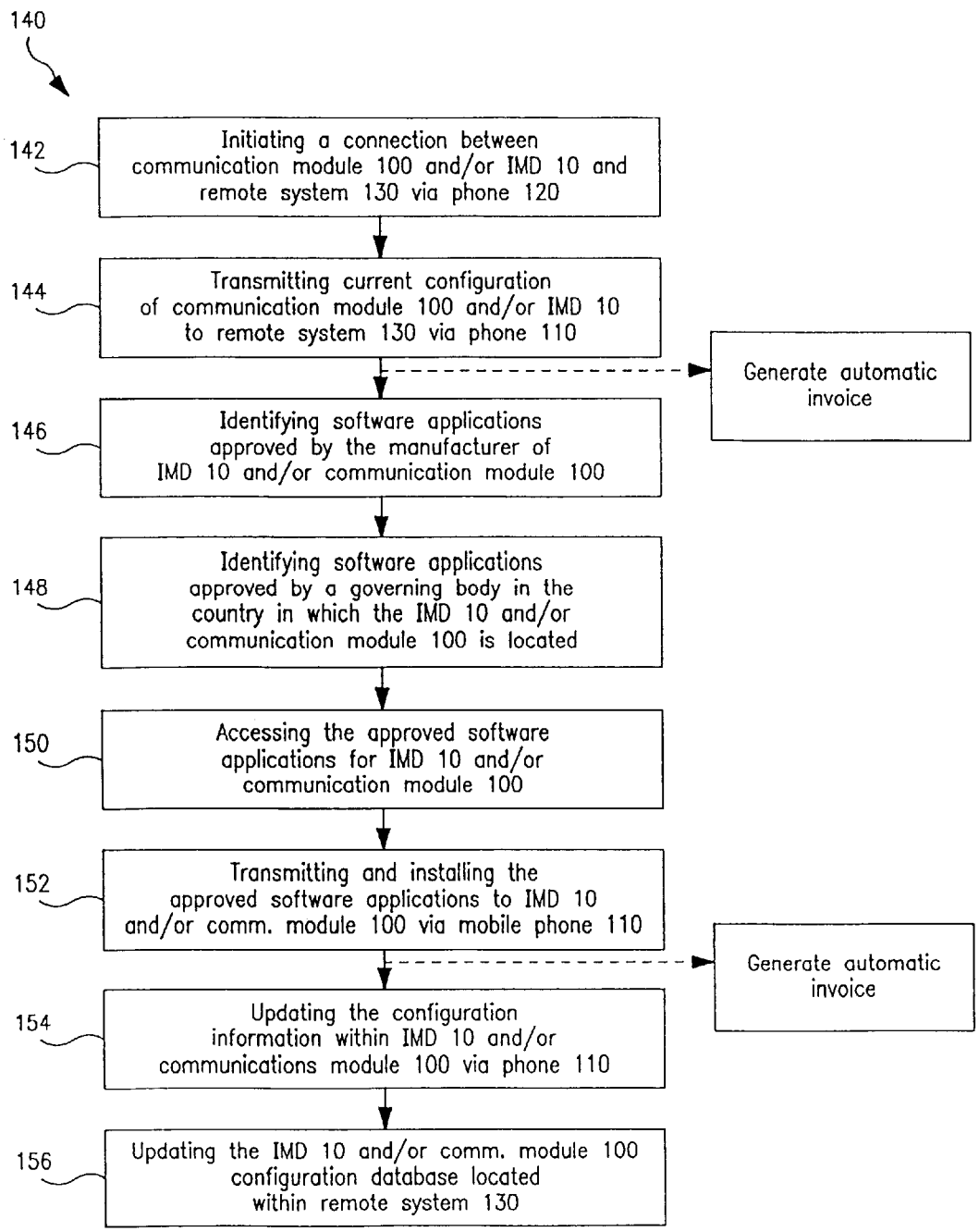
FIGS. 12B and 12C show two methods of the present invention associated with updating, debugging, downloading and/or uploading software to or from IMD 10 in accordance with the systems and devices of the present invention.
Figure 12C:
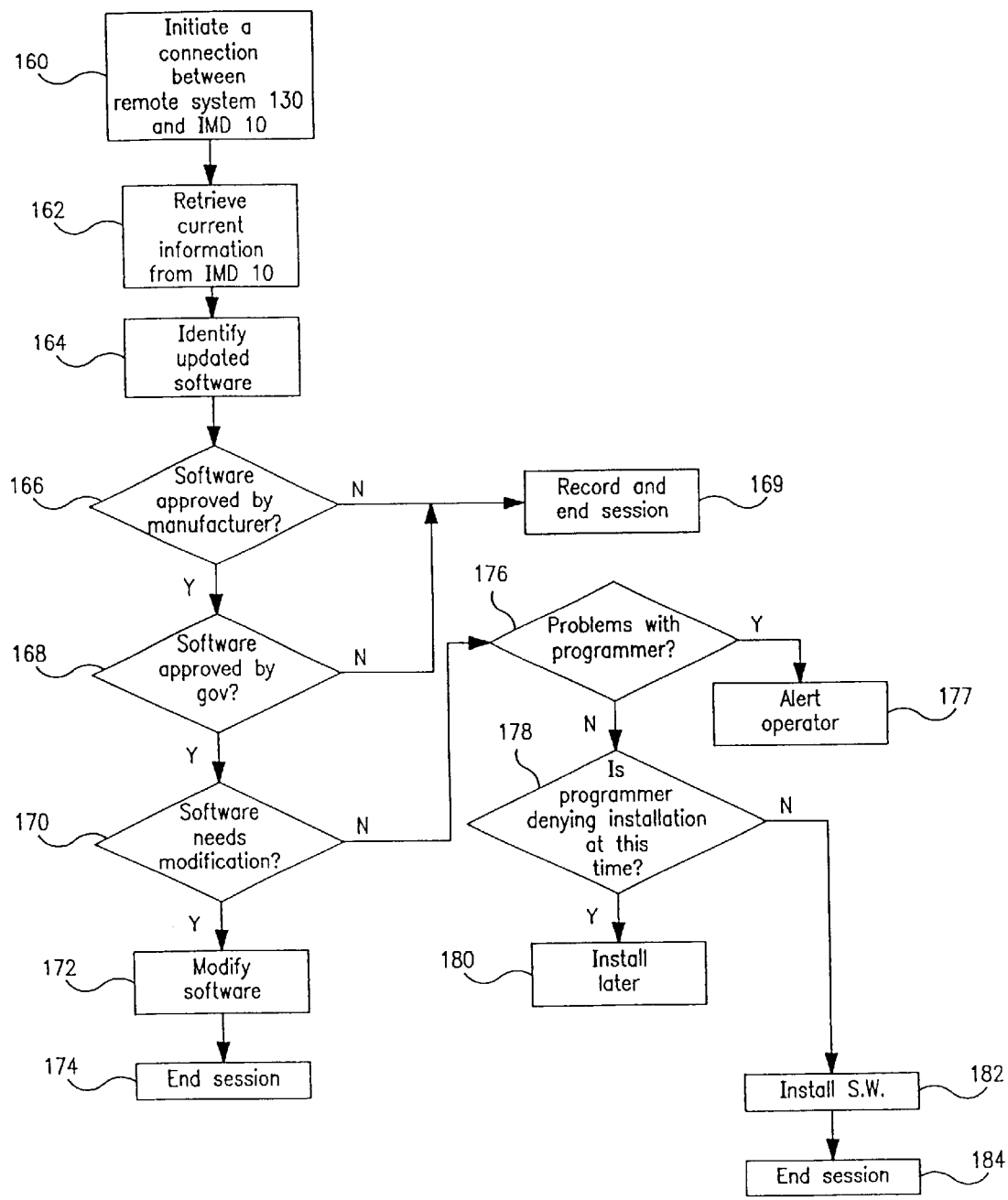

Referring now to FIGS. 12A, 12B and 12C together, remote expert data center 131 is most preferably a web-based data resources and expert system. Accordingly, data resource system 112 is a sub-component of remote data center 131. Data resource system 112 may comprise communication manager management module 124 (which preferably controls and optimizes bi-directional data communications between mobile telephone or PDA 110 and communication module 100), programmer configuration database 126, released software database 128 and rule set database 133. Those databases and module may be employed to store software upgrades, which in turn may be transmitted to mobile telephone or PDA 110 and communication module 100 and/or IMD 10 via one or a combination of the various communication channels described above.

It is preferred that remote system 130 and data resource system 112 comprise a high speed computer network system, and that remote system 130, remote expert data center 131 and communication system 130 be capable of bi-directional data, voice and video communications with communication module 100 via any of the various communications links discussed hereinabove (or combinations thereof). Remote system 130 and/or data resource system 112 are preferably located in a central location, equipped with one or more high-speed web-based computer networks, and manned 24-hours-a-day by remote health care providers 136, physicians 135, operators 136 and/or clinical personnel 136 specially trained to provide web-based remote clinical, diagnostic, and/or software services to patient 5, communication module 100 and/or IMD 10.

Continuing to refer to FIGS. 12A, 12B and 12C, communication module configuration database 126 may include information and data specifying both the hardware configuration and the software applications or programs installed in various communication modules 100, mobile telephones or PDAs 110, and/or IMDs 10 located anywhere in the world. For example, communication module configuration database 126 may contain information such as the amount of RAM contained in a particular communication module 100 and/or IMD 10, or the particular set of communication protocols and systems that may be employed to communicate with, re-program or upgrade the software contained in a particular communication module 100, mobile telephone or PDA 110, and/or IMD 10. Depending upon the amount of RAM residing in communication module 100, mobile telephone or PDA 110, and/or IMD 10, for example, it may be required that a given software application be modified prior to installation to ensure compatibility between communication module 100, mobile telephone or PDA 110, and/or IMD 10 and the software application that is to be installed. Manager module 124 then executes such software modifications prior to software installation.

It is preferred that release software database 128 be a software database which includes all current software applications or programs developed and configured for various communication modules 100 and/or IMDs 10. It is also preferred that rule set database 133 be a database containing information and data related to specific rules and regulations regarding various software applications for communication module 100 and/or IMD 10. For example, rule set database 133 may contain information concerning whether a particular software application may or may not be released and installed in an IMD 10 implanted within a patient 5 located in a particular country, or whether a software application may or may not be installed due to a lack of approval by a governing body (such as an governmental agency or regulatory branch). Rule set database 133 may also contain information concerning whether the manufacturer, owner, licensee or licensor of a software application has approved installation of the software application into communication module 100 and/or IMD 10.

Referring now to FIGS. 12B and 12C, an operator located at, near or remote from remote computer system 130 may interrogate one or more communication modules 100, mobile telephones or PDAs 110, and/or IMDs 10, or may pre-program an interrogation schedule for one or more communication modules 100, mobile telephones or PDAs 110, and/or IMDs 10 to be interrogated, by remote system 130 via communication system 120 for any of a variety of reasons. For example, it may be desired to retrieve clinical or diagnostic data or information from many IMDs 10 of a similar type and transfer such information to remote system 130 and/or data resource system 112 for storage or later evaluation in a clinical study. Alternatively, it may be desired to retrieve diagnostic or performance data from IMD 10 and/or communication module 100 on an as-required or basis or according to a predetermined schedule.

In a preferred embodiment of the present invention, and regardless of the purpose for which communication module 100 and/or IMD 10 is connected with or interrogated by remote system 130, remote system 130 and/or data resource system 112 may be configured to automatically review the various hardware configurations and software applications contained in communication module 100 and/or IMD 10. Updated software applications may therefore be installed automatically, if available and approved for installation in a particular communication module 100 and/or IMD 10. In some cases, such software installation may be a byte level update to software already residing in the communication module 100 and/or IMD 10. In other cases, such software installation may comprise replacing an outdated software application with a new application. In one method of the present invention, remote health care provider 136 is presented with the choice of whether or not to proceed with the installation of new software applications. Remote health care provider 136 may also disable or defer installation of new or updated software if communication module 100 is detected as communicating with IMD 10. Such a safety feature helps prevent interference with communications between communication module 100 and IMD 10.

Accordingly, in some embodiments of the present invention there are provided methods and processes by which remote system 130, acting through communication system 120, mobile telephone or PDA 110 and/or communication module 100, may monitor the health of patient 5, the performance and operation of IMD 10, and further debug, update and program IMD 10, most preferably through the use of a web-based globally distributed smart system. As shown in FIG. 12B, and in accordance with the teachings set forth hereinabove, invoices may be generated at various points in the methods of the present invention illustrated in FIGS. 12B and 12C.

Some embodiments of the present invention may transmit automated software updates from an expert data center to globally distributed IMDs 10 implanted in patients 5, most preferably through a web-based communication system 120. Remote system 130 comprising a globally accessible expert data center may be configured to serve individual ambulatory patients having IMDs 10 implanted within them who are located anywhere in the world where mobile telephone coverage is provided. This feature of the present invention provides significant benefits to patients. Moreover, the Internet compatible, preferably web-based expert data center may be implemented to upgrade, update, correct and modify the operational and functional software of communication module 100, which in turn may upgrade the IMD 10 by downloading thereto the required software applications or updates.

Figure 13A:
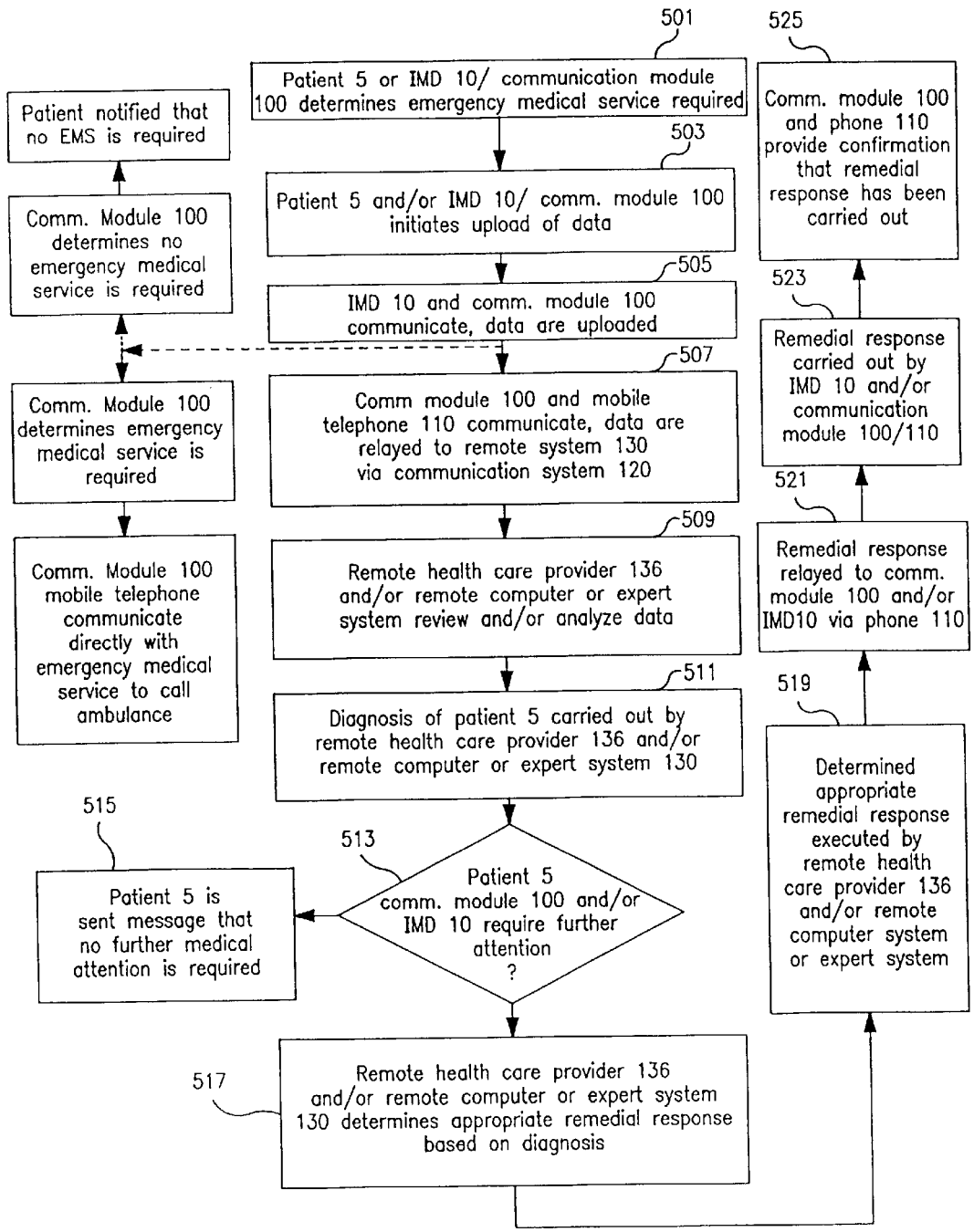
FIGS. 13A and 13B show flow charts for two methods of the present invention relating to emergency-initiated communication between IMD 10 and/or communication module 100/mobile telephone or PDA 110 and various components of remote system 130 via communication system 120.
Figure 13B:
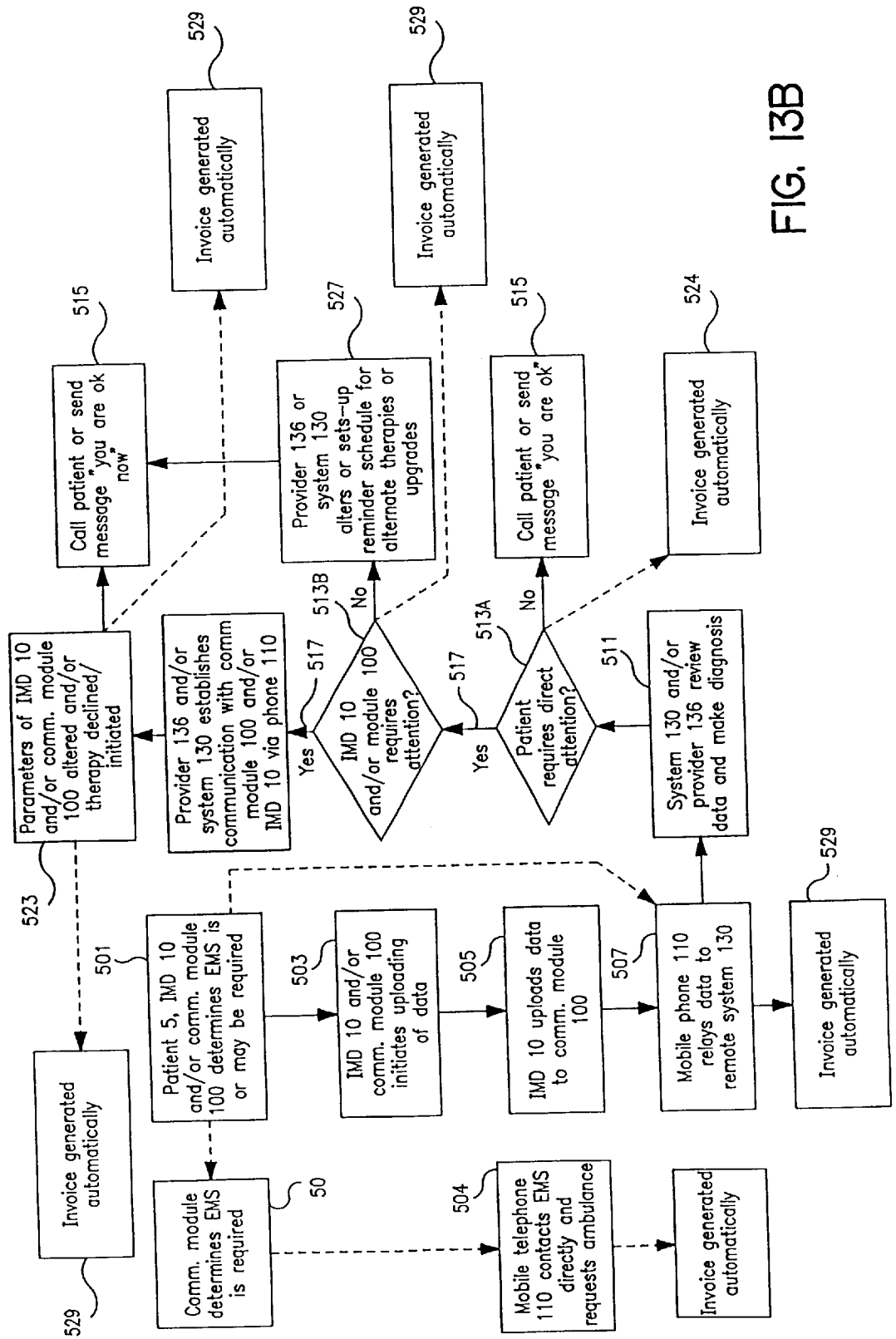

We refer now to FIGS. 13A and 13B, where flow charts for two methods of the present invention relating to emergency-initiated communication between IMD 10 and/or communication module 100/mobile telephone or PDA 110 and various components of remote system 130 via communication system 120 are illustrated. It is contemplated in FIGS. 13A and 13B that a PDA, PDA-capable mobile telephone or PDA-type device be optionally employed, either as a replacement for mobile telephone 110, in addition to mobile telephone 110 or as part of mobile telephone 110.

In FIG. 13A, patient 5, IMD 10 and/or communication module 100/mobile telephone or PDA 110 at step 501 determines or desires that emergency medical attention should be provided or is required. Such a determination or desire may be based on physiological events which patient 5 or others in his company sense, may be based upon the patient's feeling or desire that his health status or the performance status of his IMD 10 ought to be checked immediately, or upon physiological events sensed in patient 5 by IMD 10.

At step 503, patient 5, device 10 and/or communication module 100 or mobile telephone or PDA 110 initiates upload of data from IMD 10 to communication module 100. IMD 10 and communication module 100 then communicate with one another and the data are uploaded. Alternatively, step 503 may be skipped if the desired data have already been uploaded by communication module 100 and are now stored in memory/storage medium 105.

Next, at step 507, the data are transferred from communication module to mobile telephone or PDA 110, and thence on to remote system 130 via communication system 120. At step 509, remote health care provider 136, remote computer system 131 and/or 131', and/or a remote expert computer system evaluate, review and analyze the data. In step 511, diagnosis of the patient's condition (and/or that of IMD 10, communication module 100, and/or mobile telephone or PDA 110) is made by one or more of remote health care provider 136, remote computer system 131 and/or 131', and/or a remote expert computer system.

At step 513, any one or more of remote health care provider 136, remote computer system 131 and/or 131', and/or a remote expert computer system determines, on the basis of the analysis, whether patient 5, communication module 100, mobile telephone or PDA 110 and/or IMD 10 require further attention, correction or intervention. If the analysis reveals that patient 5, communication module 100, mobile telephone or PDA 110 and/or IMD 10 is or are functioning normally within acceptable limits, patient 5, IMD 10 and/or communication module 100/mobile telephone or PDA 110 may be so notified via communication system 120, mobile phone 110 such as by, for example, a visual display or audio signal emitted by communication module 100 (or mobile phone or PDA 110).

If, on the other hand, the analysis reveals that a problem exists in respect of any one or more of IMD 10, communication module 100, mobile telephone or PDA 110, and/or patient 5, then remote system 130 and/or health care provider 136 determines an appropriate remedial response to the problem, such as changing the operating parameters of IMD 10, communication module 100 and/or mobile telephone or PDA 110, delivering a therapy to the patient (e.g., a pacing, cardioverting or defibrillating therapy, or administration of a drug or other beneficial agent to patient 5), or instructing patient 5 by audio, visual or other means to do something such as lie down, go to the hospital, call an ambulance, take a medication, or push a button.

The remedial response or therapy determined in step 517 is next executed at step 519 by remote health care provider 136 or remote system 130 and relayed at step 521 via communication system 120 to communication module 100 and/or IMD 10 via mobile phone or PDA 110. After the remedial response or therapy has been delivered, at step 525 communication module and/or mobile telephone 110 may send a confirmatory message to remote system 130 and/or remote care giver 136 indicating that the remedial response or therapy has been delivered to patient 5 and/or IMD 10. Communication module 100 and/or mobile telephone or PDA 110 may also store data concerning the patient-initiated chain of events described above so that the data may be later retrieved, analyzed, and/or a future therapy determined at least partially on the basis of such data. Such data may also be stored by remote data system 130 for later retrieval, analysis and/or future therapy determination.

It is to be noted that all steps illustrated in FIG. 13A need not be carried out to fall within the scope of the present invention. Indeed, it is contemplated in the present invention that some steps illustrated in FIG. 13A may be eliminated or not carried out, that steps illustrated in FIG. 13A may be carried out in an order different from that shown in FIG. 13A, that steps other than those explicitly illustrated in the Figures may be inserted, and that steps illustrated in different Figures set forth herein (i.e., FIGS. 9A, 9B, 9C, 10A, 10B, 11A, 11B, 12a, 12B, 12C and 13B) be combined in various combinations and permutations, and nevertheless fall within the scope of certain embodiments of the present invention. The same considerations hold true for all flow charts and methods illustrated in the drawings hereof and described herein.

In FIG. 13B, some of the same steps shown in FIG. 13A are executed. Invoice generation steps 529 may be automatically generated in conjunction with or in response to one or more of steps 501, 504, 507, 513A, 513B, 517, 523 or 527 being carried out. The invoices so generated may be electronically transmitted to appropriate locations for further processing and billing. The amounts of the invoices so generated may depend, for example, on the number, type and/or frequency of services provided to patient, the type or identification indicia stored in communication module 100 or IMD 10, and other factors.

In the methods illustrated in FIGS. 13A and 13B it is further contemplated that the patient be alerted by audio or visual means that no emergency treatment of her condition is required if an erroneous or unnecessary request for emergency treatment is initiated by patient 5, that communication module 100 and/or mobile telephone or PDA 110 alert patient 5 through audio or visual means that the patient is required to take a particular action such as pressing an appropriate button or calling an ambulance when an emergency health condition has been detected, and that communication module 100 and/or mobile telephone or PDA 110 dial 911 when an emergency health condition has been detected.

In the devices and methods illustrated in the various Figures hereof, it is further contemplated that a prescription table particular to patient 5 be stored in IMD 10, communication module 100, mobile telephone or PDA 110, and/or remote system 130 that may be quickly and readily read, activated or deactivated, implemented or updated; that a remote health care provider 136 may prescribe an initial therapy, drug dosage or drug prescription regime or range for patient 5 that may later be adjusted, reprogrammed or changed remotely after data acquired in IMD have been remotely analyzed; that a remote health care provider 136 or remote system 130 may track the history of the programming of IMD 10 and archive data retrieved from IMD 10; that a remote health care provider 136 or remote system 130 may also track the history of the programming of device IMD, create corresponding patient history files, and sell same to physicians, insurance companies and/or reimbursement authorities; and that a patient's condition be monitored and followed remotely such as, by way of example only, checking the minute ventilation status of a patient in an ALS disease clinical where the progression of ALS disease is being monitored remotely.

It is to be noted that the present invention is not limited to use in conjunction with implanted defibrillators or pacemakers, but may be practiced in conjunction with any suitable implantable medical device including, but not limited to, an implantable nerve stimulator or muscle stimulator such as those disclosed in U.S. Pat. No. 5,199,428 to Obel et al., U.S. Pat. No. 5,207,218 to Carpentier et al. and U.S. Pat. No. 5,330,507 to Schwartz, an implantable monitoring device such as that disclosed in U.S. Pat. No. 5,331,966 issued to Bennet et al., an implantable brain stimulator, an implantable gastric system stimulator, an implantable vagus nerve stimulator, an implantable lower colon stimulator (e.g., in graciloplasty applications), an implantable drug or beneficial agent dispenser or pump, an implantable cardiac signal loop or any other type of implantable recorder or monitor, an implantable gene therapy delivery device, an implantable incontinence prevention or monitoring device, or an implantable insulin pump or monitoring device, and so on. Moreover, a wide variety of communication methods, protocols and techniques may be employed in various portions of the communication systems of the present invention, including, but not limited to, optical, electro-optical, magnetic, infrared, ultrasonic and hard-wired communication means.

Thus, the present invention is believed to find wide application in almost any appropriately adapted implantable medical device. Indeed, the present invention may be practiced in conjunction with any suitable non-implanted medical device, such as a Holter monitor, an external EKG or ECG monitor, an external cardiac signal loop recorder, an external blood pressure monitor, an external blood glucose monitor, a temporary cardiac pacing system having an external pulse generator, and the like.

For example, the present invention includes within its scope a system comprising an implantable medical device capable of bi-directional communication with a communication module located outside the patient, the communication module in turn being capable of bi-directional communication with a remote system via a mobile telephone, the system further comprising at least one implantable or non-implantable device operably connected to, implanted within or associated with the patient, the device being capable of bi-directional communication with the communication module. In such a manner, multiple physiologic signals, events or statuses of the patient may be monitored or controlled remotely through the communication module and the mobile telephone.

Although specific embodiments of the invention are described here in some detail, it is to be understood that those specific embodiments are presented for the purpose of illustration, and are not to be taken as somehow limiting the scope of the invention defined in the appended claims to those specific embodiments. It is also to be understood that various alterations, substitutions, and modifications may be made to the particular embodiments of the present invention described herein without departing from the spirit and scope of the appended claims.

In the claims, means plus function clauses are intended to cover the structures and devices described herein as performing the recited function and their equivalents. Means plus function clauses in the claims are not intended to be limited to structural equivalents only, but are also intended to include structures and devices which function equivalently in the environment of the claimed combination.

All printed publications, patents and patent applications referenced hereinabove are hereby incorporated by referenced herein, each in its respective entirety.

We claim:

1. A method for remotely delivering patient requested medical services to an implantable medical device over a communications system, comprising:
   establishing communications between an implantable medical device and a health care provider remote from the implantable medical device;
   requesting medical services by a patient and initiating upload of data from the implantable medical device;
   uploading data from a communications module in the implantable medical device;
   analyzing data that have been uploaded from the communications module by a remote system;
   diagnosing the patient by a remote system coupled to a health care provider;
   determining an appropriate remedial response by the health care provider based on the diagnosis;
   executing a medical response that was determined to be appropriate by the health care provider;
   confirming that the remedial response has been successfully executed in the implantable medical device; and
   generating an invoice by the health care provider for the executed medical response.

2. The method of claim 1 further comprising:
   storing implantable medical device data when the patient requests medical services to be used during diagnosing the patient to improve the diagnosis.

3. The method as in claim 1 wherein the remedial response determined to be appropriate by the health care provided is selected from the group consisting of patient monitoring, clinical study monitoring, tachycardia therapy, and requesting the patient to take medication.

4. A system for remotely delivering patient requested medical services to an implantable medical device over a communications system, comprising:
   means for establishing communications between an implantable medical device and a health care provider remote from the implantable medical device;
   means for requesting medical services by a patient and initiating upload of data from the implantable medical device;
   means for uploading data from a communications module in the implantable medical device;
   means for analyzing data that have been uploaded from the communications module by a remote system;
   means for diagnosing the patient by a remote system coupled to a health care provider;
   means for determining an appropriate remedial response by the health care provider based on the diagnosis;
   means for executing a medical response that was determined to be appropriate by the health care provider;
   means for confirming that the remedial response has been successfully executed in the implantable medical device;
   means for generating an invoice by the health care provider for the executed medical response; and
   means for storing implantable medical device data when the patient requests medical services to be used during diagnosing the patient to improve the diagnosis.

* * * * *